(12) United States Patent
Carvey et al.

(10) Patent No.: US 7,393,335 B2
(45) Date of Patent: Jul. 1, 2008

(54) METABOLICALLY EFFICIENT LEG BRACE

(76) Inventors: Matthew R. Carvey, 26 Sweeney Ridge Rd., Bedford, MA (US) 01730-1298; Andrew W. Carvey, 26 Sweeney Ridge Rd., Bedford, MA (US) 01730-1298; Philip P. Carvey, 26 Sweeney Ridge Rd., Bedford, MA (US) 01730-1298; Nicholas S. Howard, 7 Daniels Dr., Bedford, MA (US) 01730

( * ) Notice: Subject to any disclaimer, the term of this patent is extended or adjusted under 35 U.S.C. 154(b) by 0 days.

(21) Appl. No.: 11/120,503

(22) Filed: May 3, 2005

(65) Prior Publication Data
US 2005/0251079 A1 Nov. 10, 2005

Related U.S. Application Data

(60) Provisional application No. 60/568,773, filed on May 6, 2004.

(51) Int. Cl.
*A61F 5/00* (2006.01)
(52) U.S. Cl. .......................................... 602/26; 602/16
(58) Field of Classification Search ................... 602/26, 602/24, 5, 16, 20–29, 62; 632/39–40, 42–45, 632/27, 30; 482/4, 51, 901; 601/35; 607/62, 607/66; 700/245, 253; 318/568.11, 568.12, 318/568.17; 701/23; 901/23, 24; 128/878, 128/892
See application file for complete search history.

(56) References Cited

U.S. PATENT DOCUMENTS

| | | | | |
|---|---|---|---|---|
| 2,010,482 A | * | 8/1935 | Cobb | 623/31 |
| 2,632,440 A | * | 3/1953 | Hauser et al. | 602/16 |
| 3,315,406 A | * | 4/1967 | Ryan | 446/299 |
| 4,413,713 A | * | 11/1983 | West | 192/223 |
| 4,771,872 A | * | 9/1988 | Kampf | 192/28 |
| 5,011,136 A | | 4/1991 | Rennex | |
| 5,052,379 A | * | 10/1991 | Airy et al. | 602/16 |
| 5,230,700 A | | 7/1993 | Humbert et al. | |
| 5,476,441 A | * | 12/1995 | Durfee et al. | 602/23 |
| 5,575,764 A | * | 11/1996 | Van Dyne | 602/26 |
| 5,636,805 A | * | 6/1997 | Fukuzawa | 242/336 |
| 5,830,166 A | * | 11/1998 | Klopf | 602/16 |
| 6,024,713 A | | 2/2000 | Barney | |
| 6,471,664 B1 | * | 10/2002 | Campbell et al. | 602/16 |
| 6,500,138 B1 | | 12/2002 | Irby et al. | |
| 6,666,796 B1 | | 12/2003 | MacCready, Jr. | |
| 6,834,752 B2 | | 12/2004 | Irby et al. | |
| 7,153,242 B2 | * | 12/2006 | Goffer | 482/66 |
| 2002/0094919 A1 | | 7/2002 | Rennex et al. | |
| 2003/0062241 A1 | | 4/2003 | Irby et al. | |

FOREIGN PATENT DOCUMENTS

DE 44 00 820 A 1 7/1995
WO WO 94/09727 5/1994

* cited by examiner

*Primary Examiner*—Justine R Yu
*Assistant Examiner*—Shumaya B Ali
(74) *Attorney, Agent, or Firm*—Proskauer Rose LLP

(57) ABSTRACT

Embodiments of the invention relate to walking/running braces and to devices for enhancing locomotion, specifically human bipedal locomotion. More particularly, it relates to a controlled mechanical device which provides support of the torso via the hip sockets, reduces the metabolic energy associated with walking/running and reduces the incidence of falls caused by insufficient leg thrust. Embodiments of the invention also relates to reducing the strain and metabolic energy consumption associated with walking/running with a heavy backpack or other significant carried load.

13 Claims, 6 Drawing Sheets

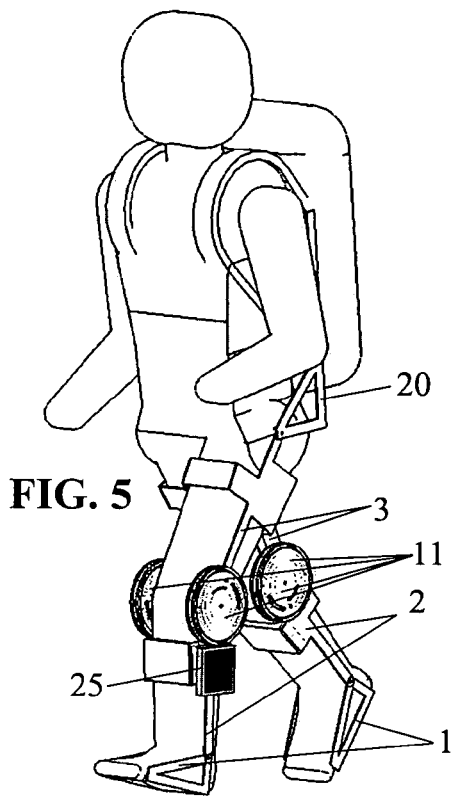
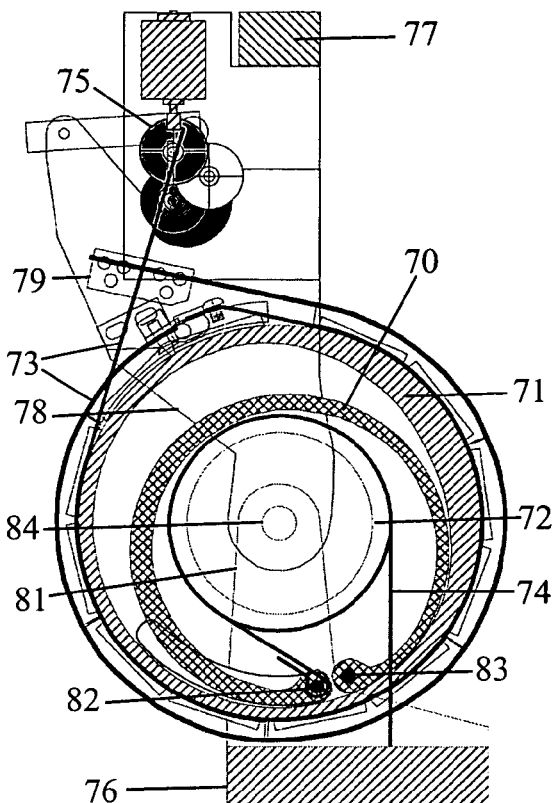
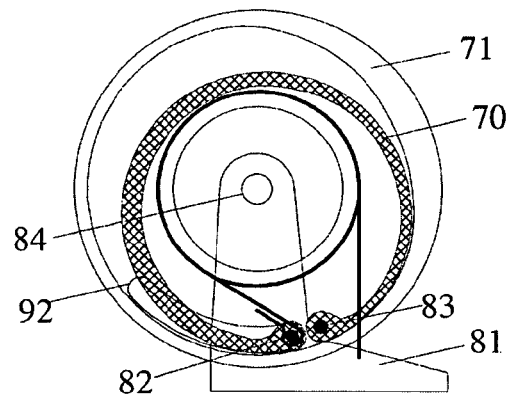
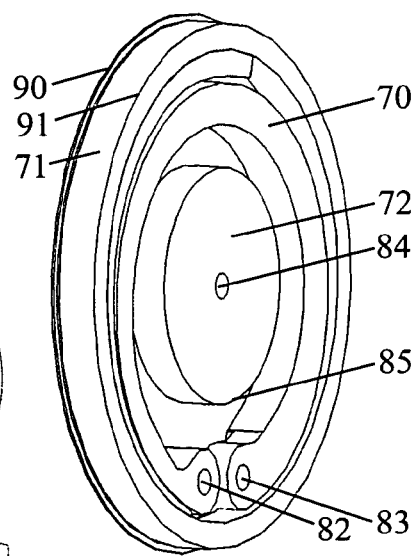
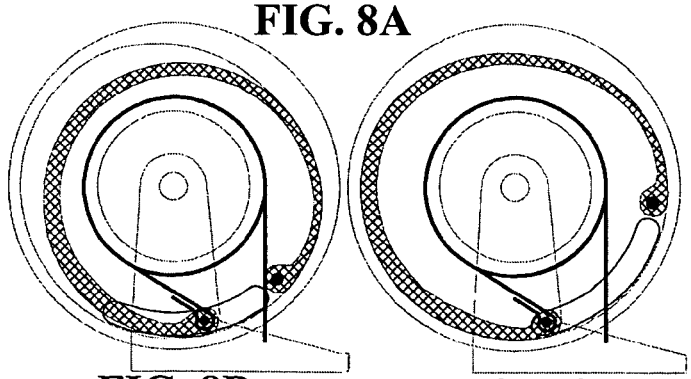

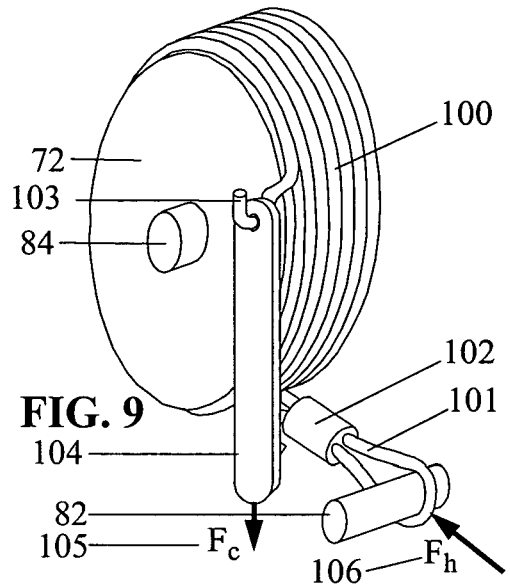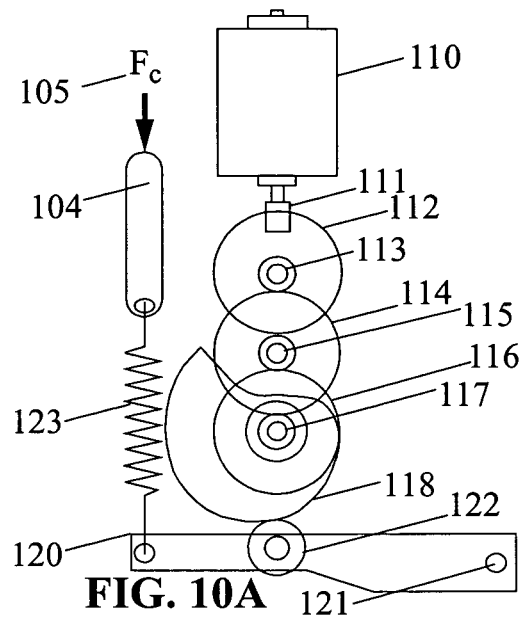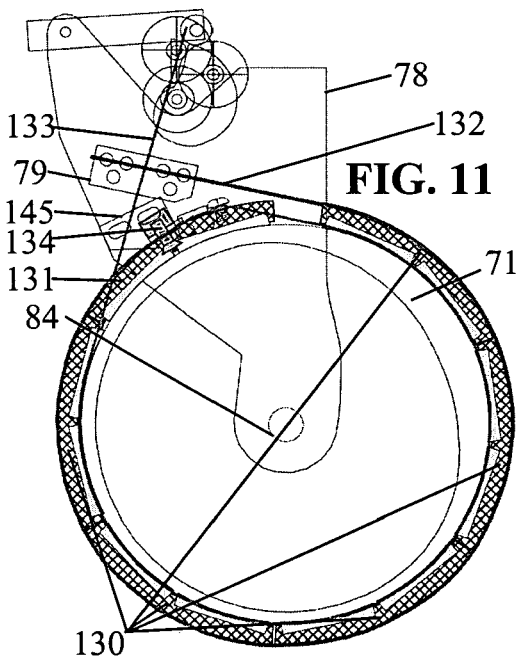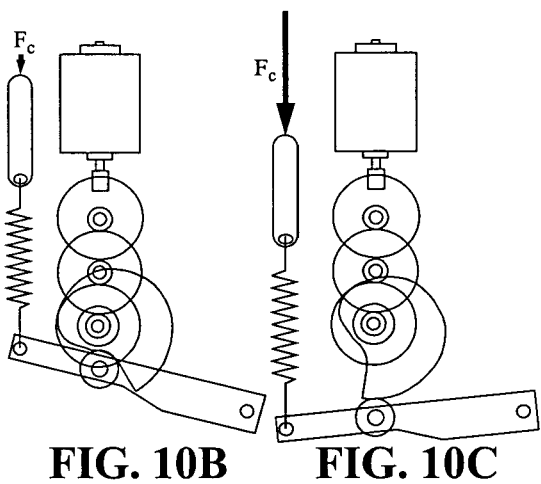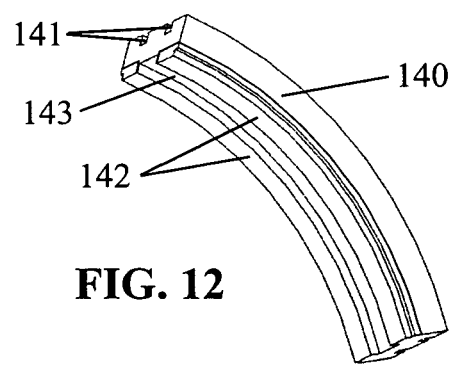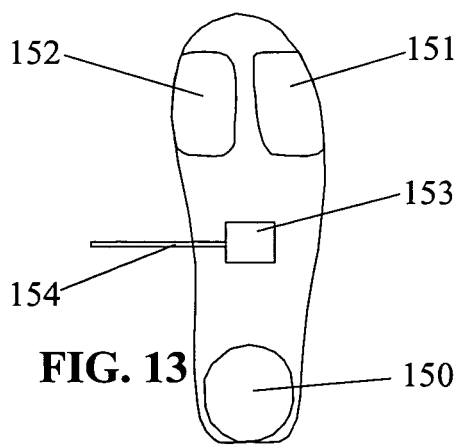

Horizontal Position of
Torso (meters)

Horizontal Position of
Torso (meters)

Horizontal Position of
Torso (meters)

METABOLICALLY EFFICIENT LEG BRACE

RELATED APPLICATION

This application claims the benefit of U.S. Provisional Application No. 60/568,773, filed on May 6, 2004, the entire teachings of which are herein incorporated by reference.

BACKGROUND OF THE INVENTION

Ground Reaction Force (GRF) is defined as a force vector applied by the ground to a person at a point on a person's footprint called the Center of Pressure (COP). The GRF direction can be modeled by a force vector colinear with a line connecting ankle and hip. Neglecting air friction, the average horizontal component of the GRF must exactly equal zero for a person walking/running at constant average velocity regardless of ground slope. If this were not the case, then a person's torso would increase or decrease its average horizontal velocity. Similarly, the average vertical component of the GRF must be exactly equal to body weight regardless of the ground slope. If this were not the case, then the average distance from the torso to the ground would increase or decrease.

The function of the legs in human bipedal locomotion (hereafter locomotion) is to make periodic ground contact with a foot during each step for the purpose of transferring the GRF to the torso. By making the average horizontal GRF less than or greater than zero, the torso can be accelerated or decelerated. The locomotion process is one whereby the torso weight is supported alternately between one leg and the other. Each step consists of a support epoch during which one leg supports the torso weight while the alternate leg is swinging forward preparing for the next step. Each support epoch is followed by a transition epoch where the torso weight transitions between the current support leg to the new support leg.

Others have created locomotion assist devices throughout recorded history mostly with the intention of mitigating leg dysfunction. Locomotion assist devices are currently in widespread use today in the form of crutches, canes, and a variety of knee braces. Some locomotion assist devices include wheeled devices, such as bicycles, wheelchairs, scooters, and other alternatives to human bipedal locomotion. These devices transfer the GRF to the torso from points on the ground which are constantly moving.

Canes and crutches are devices that allow a user to transfer a portion (up to all) of the GRF to the torso via the arm sockets. These devices are effective in reducing the gait problems caused by one or both dysfunctional legs and are commonly employed. Unfortunately these devices are problematic for long term use, over uneven terrain, or where the arm sockets are not suitable for transferring substantial portions of the GRT to the torso.

Locking knee braces are another class of device commonly used to transfer the GRF to the torso. Unlike canes and crutches, locking knee braces transfer the GRF to the torso via the hip sockets. Since this is the normal mechanism for humans to transfer GRF to the torso, it is a preferred mechanism. Common locking knee braces consist of a shank and thigh frame coupled together with a hinge that can be locked at an explicit knee angle when torso support is required. Knee braces are widely used to reduce knee joint stresses and provide knee immobilization following surgery. In general they are not employed as walking enhancement devices because the fixed knee angle greatly impedes normal action of the leg during walking/running.

There exists several intelligent, electronic knee braces used to control resistive torque or damping about the knee joint. These knee braces are primarily intended to mitigate leg dysfunction caused by amputation. Using sensory information, these active braces can discriminate between early and late support phases thereby allowing amputees to flex their knee just after heel strike. This feature is important for shock absorption and is not possible with prior mechanically passive prosthesis. Electronic knees can also supply different levels of damping during swing and support dependent on walking speeds using adaptive algorithms. Several of these electronically controlled knee braces have been commercialized, such as the Otto Bock's C-leg and Ossur's Rheo Knee.

U.S. Pat. Nos. 6,500,138, 6,834,752, and U.S. Patent Publication 2003/0062241 disclose a knee brace which provides support while allowing unimpeded knee angle flexion during leg swing. This device, called an auto-locking knee brace, employs a microprocessor controlled one-way clutch at the knee joint of a common knee-ankle-foot-orthotic. This device has two modes of operation. In one mode, the one-way clutch is inactivated thereby allowing free rotation of the foot/shank and thigh frames. One-way clutches have a well known property that when activated they have an easy rotation direction where only a small amount of torque can be coupled from input to output and a hard direction where an arbitrarily large amount of torque can be coupled from input to output. This feature of the one-way clutch is exploited in the auto-locking brace to allow relatively unimpeded leg extension prior to heel strike while providing full support following heel strike. Activation of the one-way clutch utilizes a solenoid. For polio and stroke patients, the auto-locking knee has shown significant improvements including reducing metabolic energy consumption of wearers of the device.

Numerous mobility assist devices have been developed over the years employing mechanisms which incorporate means for temporarily storing and releasing the energy generated and needed during each step. U.S. Pat. Nos. 420,178 and 420,179 disclosed a device employing bow springs attached to a shoulder and a pelvis. The '179 Patent incorporates a foot-lift mechanism to enable swing leg foot clearance, however does not teach a workable mechanism for activating the foot-lift mechanism.

U.S. Pat. No. 4,872,665 discloses a running brace that employs a telescoping gas spring and a swing leg foot clearance mechanism employing a ratchet joint. The disclosure does not discuss practical methods for release of the ratchet joint. The primary problem with the device is there is no mechanism for controlling the natural release of the energy stored in the gas spring phase locked to the gait cycle selected by the wearer. In particular, assuming that an embodiment of the device is possible, a wearer must adjust his gait cycle to the natural frequency dictated by the physical parameters of the device.

U.S. Pat. No. 5,016,869 discloses a running assist device for enhanced mobility and reduced metabolic energy consumption. In this device, the GRF is coupled to the torso mass directly through the legs without any mechanism working in parallel with the legs. Accordingly, the device cannot store energy available during the period of time when the distance between hip socket and ankle is decreasing. In effect, the device acts as a mechanism for transferring GRF to the soles of the wearer's feet, not the torso.

U.S. Pat. Nos. 4,967,734, 5,011,136, and U.S. Patent Publication 2002/0094919, disclose energy-efficient running braces employing a mechanical spring which temporarily stores the energy during the period when the distance between torso center of mass and the ground is decreasing and releases the energy during the period when that distance is increasing. These devices support the torso via a torso harness and refer to means for generating a constant leg thrust. Measurement of the GRF reveal that the required leg thrust increases substantially as running speed is increased, reaching up to five times body weight during sprinting. Benefits of these devices do not appear to be achievable by a wearer suffering single leg dysfunction. The devices also appear to require extensive periods of time to doff and don. All of the above-mentioned designs couple the GRF to the torso via a torso harness.

SUMMARY OF THE INVENTION

One embodiment of the invention supports the torso by fixing one arm of a torsion spring to a shank frame and coupling the other arm of the torsion spring to a thigh frame. The shank and thigh frames are coupled to the wearer's shank and thigh via padded half shells and Velcro straps. The shank and thigh frames are passively hinged at the knee axis. This configuration supports the torso by working in parallel with the wearer's legs to transfer the Ground Reaction Force (GRF) from ground to the torso via the wearer's hip sockets for all knee angles. At zero knee angle, 100% of the torso weight is supported via the wearer's leg skeleton. As the knee angle increases, the percentage of torso weight supported by an embodiment of the invention increases while the percentage supported by the wearer's leg skeleton decreases. The brace allows the wearer to supplement the torso support features of an embodiment of the invention to any extent desired via natural contracting of the wearer's quadricep muscles. Note that a conventional locking knee brace only provides this support at one knee angle and does not allow the wearer to supplement the torso support via contracting the wearer's quadricep muscles. The addition of an attached mass support frame, hinged to braces worn on both legs and shoe frames, hinged at the ankle, results in the attached mass being fully supported by the braces. Unlike torso and carried load support, support of the attached mass does not increase pressures applied by the brace to the wearer's shank and thigh.

The metabolic energy reduction benefit of an embodiment of the invention is based on the observation that during each gait cycle, the support leg knee flexes and extends. During support leg knee flexion, the distance between hip and ankle decreases. This results in energy being extracted from the torso. Similarly, during support leg knee extension, the distance between hip and ankle increases. This results in energy being added to the torso.

Without use of the principles of the embodiments of invention, the torso energy decrease during knee flexion is converted into heat by muscle activity of the support leg. The torso energy increase required during knee extension must be supplied from muscle activity of the support leg. With use of the principles of the embodiments of invention, most of the torso energy decrease during knee flexion is stored as potential energy in a torsion spring. Since the energy stored need not be converted into heat by the muscle activity of the support leg, the muscle activity during knee flexion is substantially reduced. During knee extension, the brace releases the stored energy of the spring. Since the energy sourced from the spring replaces most of the normal muscle activity during knee extension, overall metabolic energy is reduced.

It should be clearly understood that the brace is mechanically passive. While it employs batteries to power the sensing and control electronics, none of the energy drawn from the batteries is injected into the system. Since any physical embodiment of the invention will result in frictional and other energy losses, the brace will never be 100% efficient. Accordingly, the wearer must supply metabolic energy to compensate for these inefficiencies. Since an embodiment of the invention reduces the metabolic energy during both knee flexion and knee extension, a double benefit is gained. For example, if the brace is 83% efficient, overall metabolic energy consumption decreases by a factor of six.

When the wearer dons the brace, the simplified system comprises a spring and mass. This system results in a natural motion exclusively dictated by the physical parameters of the spring, mass and starting conditions. This natural motion would normally require that the wearer adapt his gait to the physical parameters of an embodiment of the invention. Though it has been shown experimentally that wearers of embodiments of the invention can adapt their gait to the brace, the adjustment period is fairly lengthy and the system is somewhat difficult to control.

A novel mechanism enables an embodiment of the invention to adapt to the gait selected by the wearer rather than vice versa. An embodiment employs a controlled one-way clutch to mechanically freeze the knee angle at that point where the stored energy is maximum. After the body has progressed to the optimal leg angle, the control unfreezes the energy stored in the spring. The energy of the torsion spring then naturally flows into torso. This same mechanism works identically for the attached mass.

A preferred embodiment comprises shoe frame, shank frame, thigh frame, torsion spring, two controlled one-way clutches and control electronics. The shoe frame is passively hinged to the distal end of the shank frame at the ankle joint. The distal end of the thigh frame is passively hinged to the proximal end of the shank frame at the knee joint. The shoe frame is fixed to the wearer shoe via a quick connect/disconnect mechanism. Shank and thigh frames are coupled to the wearer's shank and thigh via straps and padded shells. A mechanism called an actuated knee couples the shank and thigh frames at the knee joint. It is composed of a torsion spring in series with a one-way dual-state clutch called the thigh clutch. A second one-way dual-state clutch called the spring clutch operates in parallel with the torsion spring.

In a preferred embodiment, one arm of the torsion spring is directly coupled to the shank frame while the other end of the torsion spring is coupled to both the input arbor of the thigh clutch and the input arbor of the spring clutch. The thigh clutch output arbor is directly coupled to the thigh frame. The thigh clutch allows for torque produced by the thigh frame to be coupled to the torsion spring. The spring clutch output arbor is directly coupled to the shank frame. The spring clutch provides a mechanism for freezing the torsion spring at that point where maximum energy is stored. It should be noted that if one arm of the torsion spring is directly coupled to the thigh frame and the use of the two clutches is interchanged, identical behavior occurs.

In a preferred embodiment, many components of the shoe, shank and thigh frames as well as spring and clutches are replicated on both the inner side and outer side of the leg. Hence, a preferred embodiment employs two torsion springs, two thigh clutches and two spring clutches. One actuator is employed to control both thigh clutches and a second actuator is employed to control both spring clutches. This balanced scheme allows the large forces produced at the hip socket to be transferred to ground without creating axial torques on the brace. It should be noted that an unbalanced scheme employing only a single torsion spring, single thigh clutch and single spring clutch also implements all principles of operation of various embodiments of the invention.

In a preferred embodiment, a half cylindrical padded shell, positioned at the upper front of the wearer's shank, couples the inner and outer struts of the shank frame. This shell allows the wearer to transfer a fraction of the hip socket force to the shank frame. Similarly, a half cylindrical padded shell, positioned at the upper back of the wearer's thigh, couples the inner and outer struts of the thigh frame. This shell allows the wearer to transfer a fraction of the hip socket to the thigh frame.

One embodiment of the invention utilizes well known clutches called one-way, dual-state clutches. These clutches are characterized by having two states, activated and released. In the activated state, these clutches have a hard rotation direction and an easy rotation direction. In the hard direction a large torque can be coupled from input to output arbors before slippage occurs. In the easy direction, only a small torque can be coupled between input and output arbors before slippage occurs. The hard direction of the thigh clutch occurs during knee flexion and hard direction of the spring clutch occurs during knee extension. In the released state, approximately zero torque can be coupled between input and output arbors before slippage occurs.

The spring clutch employs a variant of a well known class of one-way clutches called spring wrap clutches. Spring wrap clutches employ a wire coiled in a helix as the means for transferring torque from input to output arbors. One end of the wire coil is fixed to the output arbor and the other end is used for control. When zero control force is applied, the input and output arbors rotate freely. When a force is applied to the control end of the wire coil, a large torque can be transferred from input to output arbors in the hard direction.

The thigh clutch employs a novel variant of the spring wrap clutch. It couples torque from the thigh frame to one arm of the torsion spring. When in the released state, the knee is free to flex and extend. When in the activated state, the wearer will experience only a small back torque when extending his knee. During knee flexion on level or ascending terrain, all of the torque produced by the thigh frame is coupled to the torsion spring without slippage. During knee flexion on descending terrain, again all of the torque produced by the thigh frame is coupled to the torsion spring, but the microprocessor allows controlled slippage. This slippage implies that the thigh clutch must be able to dissipate energy like the brakes on a bicycle.

A preferred embodiment utilizes two motor/gearbox driven CAMs to supply a force to the control side of each of the one-way clutches. In normal operation, the CAM makes one revolution for each step cycle. The control CAM has an engineered shape with several important properties. First, the control force can be varied from zero to maximum over any time period. Second, the force can be changed from maximum to zero almost instantaneously. Lastly, the shape minimizes the power drain from the battery.

In order to clarify the action of an embodiment of the invention, the concept of a Seg is introduced. A Seg is an imaginary line connecting ankle and hip. Its length and angle with respect to vertical vary throughout the step. A brief description of brace operation during level walking starts with the system just prior to the swing phase of the braced leg. This transition is detected by detecting a negative Seg angle together with a change of foot pressure to near zero. Just prior to the start of the swing phase, the spring clutch is in its released state and the thigh clutch is in its activated state. At the start of the swing phase, the thigh clutch activation CAM is rotated slightly causing a quick transition of the thigh clutch to its released state. After the transition, the wearer can easily flex the braced leg and swing it forward. Some time later, the swing leg Seg angle becomes positive and the wearer starts extending the swing leg. This initiates rotation of the CAMs until both clutches reach their fully activated states. Properly engineered, both clutches will be in their fully activated state by the time heel strike occurs. Following heel-strike, increasing flexion of the knee causes torsion spring energy to increase until the maximum knee angle is sensed. At that time, the Seg angle is recorded and stored in the microprocessor's $\beta_{crit}$ register. The hip socket of the support leg will continue to rotate at a fixed distance from the support leg ankle until the Seg angle reaches $-\beta_{crit}$. At that point, the microprocessor causes the spring clutch CAM rotate slightly causing the spring clutch to transition to released state. This action allows the energy stored in the torsion spring to be released into the system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 shows a perspective view of a person employing the embodiment of FIG. 3;

FIG. 6 shows a side view of one embodiment of an actuated knee;

FIG. 7 shows a perspective view of a transfer arbor assembly of the actuated knee of FIG. 6;

FIGS. 8A-8C shows a torsion spring relationship with the thigh clutch arbor and shank frame at three different knee angles;

FIG. 9 shows a perspective view of one embodiment of a spring clutch of an embodiment of the present invention;

FIGS. 10A-10C show elements of a spring clutch activator in its partially activated state, its fully released state and its fully activated state;

FIG. 11 shows a side view of a thigh clutch;

FIG. 12 shows a perspective view of a thigh clutch shoe;

FIG. 13 shows a sensorized insole for use in a wearer's shoe; and

DETAILED DESCRIPTION OF THE INVENTION

Figure 1:
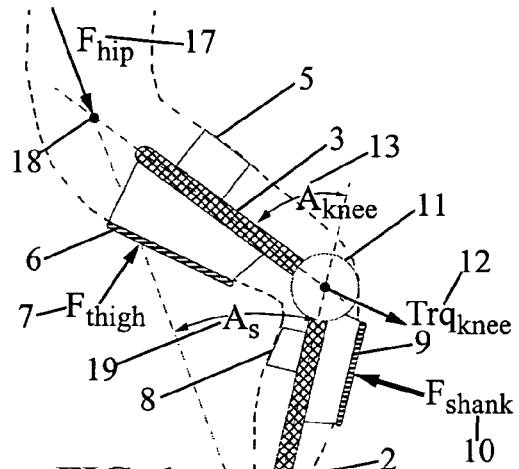
FIG. 1 shows a side view of a person wearing the one embodiment of the present invention.

A description of preferred embodiments of the invention follows.

In the following discussion, the present invention shall be referenced as a leg brace or brace. When a wearer of the present invention dons the brace, the Ground Reaction Force (GRF) is transferred to the wearer's hip socket via two parallel structures. One structure is the wearer's femur, tibia, and foot skeletal bones. The other structure is the brace's thigh, shank, and shoe frames.

One embodiment of the invention addresses the problem of supporting the torso weight, supporting the weight of a carried load, and/or supporting the weight of an attached mass while standing, walking or running on any terrain. In addition to supporting the torso/carried load/attached mass weight, an embodiment of the invention also extracts and stores energy produced by the torso and/or carried load and/or attached mass during the period when the distance from a hip socket to an ankle is decreasing and then releases the stored energy during a period when the distance from the hip socket to the ankle is increasing. An embodiment of the present invention enables a wearer to reduce the amount of metabolic energy that would be normally required by the wearer without use of the embodiment of the present invention during walking and running activities. There is also provided a control mechanism for yielding the support and reduced metabolic energy consumption benefits at any speed and step length selected by the wearer over level or descending terrain.

In another embodiment, when a user of the brace wears a conventional backpack; support of that backpack weight must originate from the user's hip sockets. In effect, carrying extra weight simply adds mass to the torso (a carried load). By adding an attached mass support frame to braces worn on each leg, the weight of an attached mass such as a backpack is supported by the leg braces and not by the user's hip sockets. An attached mass support frame is likely to be a preferred usage of an embodiment of the invention when one adds a mass to the system since it reduces the stresses created on the wearer's skeleton and joints. Following discussions will utilize the term torso to mean wearer's torso system (comprising head, thorax, pelvis, and arms), a carried load, an attached mass, or any combination of the three.

To understand the full benefits of embodiments of the present invention, it is important to understand what is meant by support. One should first visualize a torso supported by legs wearing embodiments of the invention. One or both feet make periodic contact with the ground with the purpose of maintaining a relatively fixed distance between the ground and the torso Center of Mass (COM). By providing net forward or reverse thrust on each of the legs, the torso can be accelerated, decelerated. All this can be accomplished over uneven terrain. Bipedal locomotion is a process whereby the torso weight is supported alternately between one leg and the other. In walking and running, each step consists of a support epoch during which one leg supports the torso weight while the alternate leg is swinging forward preparing for the next step. Each support epoch is followed by a transition epoch where the torso weight transitions between the current support leg to the new support leg.

Ground Reaction Force (GRF) is defined as a force vector applied by the ground to a person at a point on a footprint called the "Center of Pressure (COP)." While the COP moves from heel to toe during the support epoch, to a first order, we can approximate the COP as located directly under the ankle. Neglecting air friction, the average horizontal component of the GRF must exactly equal zero for a person walking/running at constant average velocity regardless of ground slope. Similarly, the average vertical component of the GRF must be exactly equal to body weight regardless of the ground slope. While the average values of horizontal and vertical GRF are fixed by these constraints, the magnitude and direction of the GRF vary substantially during each step period.

Numerous devices have been created to transfer the GRF to the torso. These devices include crutches, canes and leg braces. One of the most successful is the conventional knee brace. A conventional knee brace consists of a shank frame and a thigh frame coupled together with a hinge employing stops to fix the knee angle. Typically, these frames are semi-rigid, and include padded half shells with straps to provide a mechanism for coupling a wearer's shank and thigh to the brace's shank frame and thigh frame. Knee braces are widely used to reduce knee joint stresses and provide knee immobilization following surgery.

Knee braces, while widely used, are not normally employed as walking enhancement devices because they impede normal gait activity. An embodiment of the present invention extends the basic knee brace concept in several aspects and introduces the benefits of reduced metabolic energy consumption over level and downsloping terrain at wearer selectable gait speed and step lengths. These benefits are accrued while supporting the torso weight via the hip sockets. Knee brace extensions include an actuated knee joint coupling the shank frame and the thigh frame and the addition of a foot frame hinged to the shank frame. While many benefits of embodiments of the present invention result without the foot frame, incorporating both the actuated knee joint and foot frame maximizes the overall benefits.

FIG. 1 shows a side view of a person wearing the one embodiment of the present invention. The general brace includes a shank frame 2, a thigh frame 3 and an actuated knee joint 11. An alternate embodiment includes a shoe frame 1 for attaching to a wearer's shoe 4. The thigh frame 3 includes a thigh strap 5 and a padded thigh shell 6 for providing a means for coupling force $F_{thigh}$ 7 between the wearer's femur and the thigh frame 3. The shank frame 2 includes a shank strap 8 and a padded shank shell 9 for providing a means for coupling force $F_{shank}$ 10 between the wearer's tibia and the shank frame 2.

The actuated knee joint 11 produces a torque $Trq_{knee}$ 12 between the thigh frame 3 and the shank frame 2. The magnitude of $Trq_{knee}$ 12 is dependent on a knee angle $A_{knee}$ 13. Forces $F_{ankle1}$ 14 and $F_{ankle2}$ 15 are forces applied by the shoe frame 1 to the shank frame 2 at an ankle joint 16. $F_{hip}$ 17 is a force applied by the torso to the hip socket caused by the gravitational field and inertial forces. To a first order, we assume that the wearer creates no torque either at a knee or an ankle. Accordingly, $F_{hip}$ 17 has a direction pointing directly from hip socket 18 to ankle joint 16. The only direct coupling between GRF and the wearer's hip socket 18 is through the wearer's foot, tibia and femur. The brace, however, provides an indirect coupling between the GRF and the wearer's hip socket 18 which increases from zero to 100% as a function of the knee angle $A_{knee}$ 13.

To a first order, we can assume that the entire torso mass is concentrated as a point mass located at the hip socket 18 and the leg and the brace are massless. With this assumption, the support function of the one embodiment of the present invention can now be seen. At near zero shank angle $A_s$ 19, the GRF is transferred to the hip socket 18 exclusively through the wearer's skeleton. As the shank angle $A_s$ 19 increases, a portion of the GRF is transferred to the hip socket 18 directly by the wearer's skeleton and the remaining portion of the GRF is transferred to the hip socket 18 indirectly by the brace.

Figure 2A:
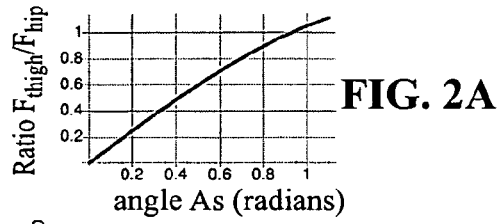
FIGS. 2A-2D show computed normalized forces at three brace/human contact areas versus ½ knee angle of a wearer of the invention of FIG. 1.
Figure 2B:
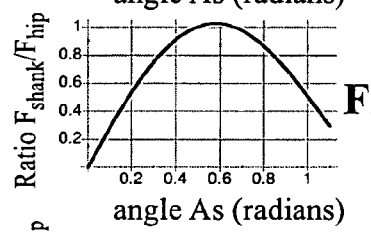
Figure 2C:
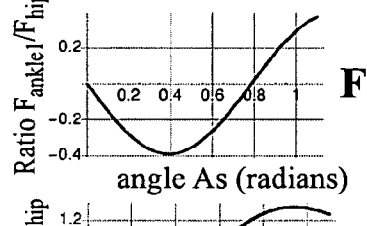
Figure 2D:
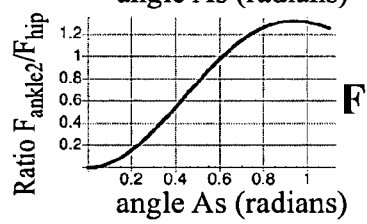

FIGS. 2A-2D show forces at three brace/human contact areas versus ½ knee angle of a wearer of the invention of FIG. 1. The forces $F_{thigh}$ 7, $F_{shank}$ 10, $F_{ankle1}$ 14 and $F_{ankle2}$ 15 are shown as functions of shank angle $A_s$ 19 as a fraction of $F_{hip}$ 17. FIG. 2A shows a normalized $F_{thigh}$ 7 force versus shank angle $A_s$ 19. As can be seen, $F_{thigh}$ 7 increases from zero to approximately 1.2 $F_{hip}$ 17 at maximum knee flexion. FIG. 2B shows a normalized $F_{shank}$ 10 force versus shank angle $A_s$ 19. As can be seen, $F_{shank}$ 10 increases from zero to approximately 1.05 $F_{hip}$ 17 at shank angle $A_s$ 19 of 0.55 and then decreases. FIG. 2C shows a normalized $F_{ankle1}$ 14 force versus shank angle $A_s$ 19. Because $F_{ankle1}$ 14 is perpendicular to the $F_{hip}$ 17 vector, there is an equal an opposite force between the wearer's foot and the wearer's shoe. As can be seen, $F_{ankle1}$ 14 first becomes negative and then becomes positive but never exceeds approximately 0.4 $F_{hip}$ 17. Lastly, FIG. 2D shows a normalized $F_{ankle2}$ 15 force versus shank angle $A_s$ 19. As can be seen, $F_{ankle2}$ 14 increases monotonically to equal $F_{hip}$ 17 at a shank angle $A_s$ 19 of approximately 0.6 radians. Since $F_{ankle2}$ 14 plus the foot force against the bottom of the shoe must equal $F_{hip}$ 17, the force of the foot against the bottom of the shoe decreases to zero at a shank angle $A_s$ 19 of approximately 0.6 radians and then becomes negative. A negative force implies that the wearer's foot applies an upward force on the top inside of the shoe. This analysis shows how the torso force applied to the hip socket 18 (FIG. 1) is indirectly supported by the brace.

Figure 3:
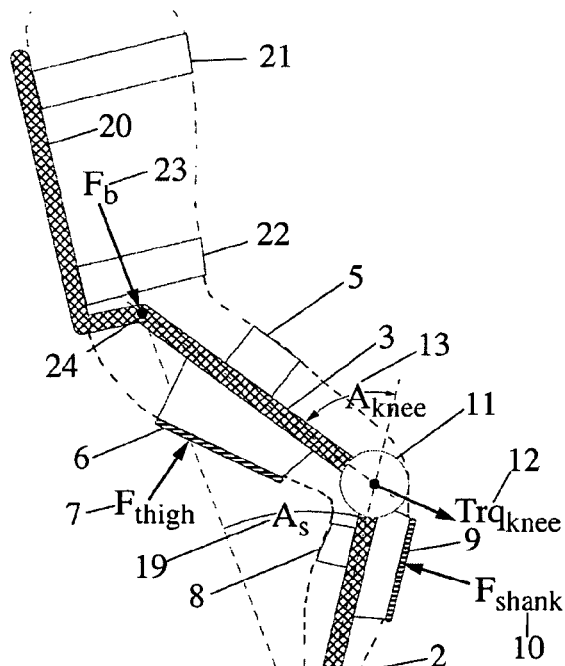
FIG. 3 shows is a side view of the invention of FIG. 1 augmented with an attached mass support frame.

FIG. 3 shows is a side view of the invention of FIG. 1 augmented with an attached mass support frame 20. The attached mass support frame 20 is hinged at a proximal end of the thigh frame 3. The attached mass support frame 20 includes chest strap 21 and waist strap 22 for providing a means for the attached mass support frame 20 to transmit inertial and gravitational forces to the wearer's torso. In addition to the chest strap 21 and waist strap 22, an attached mass support frame hinge 24 provides a means for the attached mass support frame 20 to transmit inertial and gravitational forces to the support leg brace. It is straightforward to see that if a backpack mass is concentrated at a point mass located at the attached mass support frame hinge 24, 100% of the GRF associated with the backpack is transmitted through the brace with no support via the wearer's skeletal structure. In effect, the gravitational and inertial forces of the attached mass $F_b$ 23 is added to the $F_{hip}$ 17 as an applied load to the support leg brace.

Figure 4:
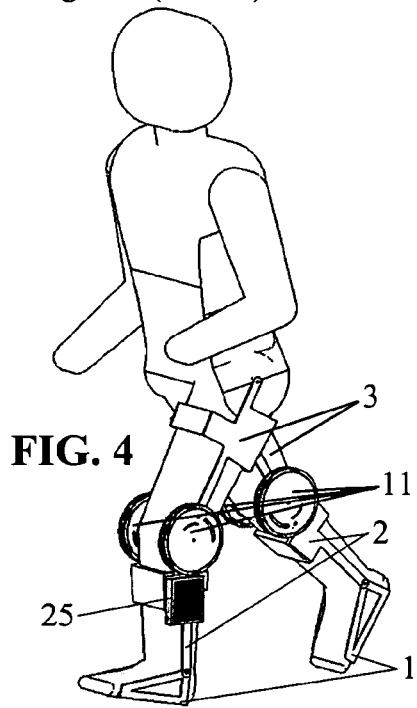
FIG. 4 shows a perspective view of a person employing the embodiment of FIG. 1 on both legs.

FIG. 4 shows a perspective view of a person employing the embodiment of FIG. 1 on both legs. Each brace includes a shoe frame 1, a shank frame 2, an actuated knee 11, a thigh frame 3, and a control module 25. Although a pair of braces is shown, it should be understood that a single brace can be employed including at least one actuated knee 11 and optionally including the shoe frame 1. As shown, both the left and right braces have similar components with mirror symmetry. The shoe frame 1 is coupled to the shank frame 2 via bilateral hinges colinear with the wearer's ankle joint 16 (FIG. 1). A proximal end of the shank frame 2 is also coupled to a distal end of the thigh frame 3 via bilateral hinges colinear with the wearer's knee joint. Each of the actuated knees 11 include two arms, one of which is fixed to the distal end of the thigh frame 3 and the other arm is fixed to the proximal end of the shank frame 2. A quick release mechanism can be employed to fix the shoe frame 1 to a wearer's shoe 4 (FIG. 1). The shank frame 2 and the thigh frame 3 are coupled to the wearer's shank and thigh using well known schemes employing straps and padded shells connecting inner and outer side struts of the respective frames. The brace control module 25 is preferably fixed to the shank frame 2.

FIG. 5 shows a perspective view of a person employing the embodiment of FIG. 3. The embodiment of FIG. 5 includes all the components of FIG. 4 coupled to an attached mass support frame 20 via hinges colinear with a wearer's hip socket 18 (FIG. 1). However the thigh frame 3 includes a quick release hinge on its outer side strut to allow hinged coupling of the thigh frame 3 to the attached mass support frame 20. The attached mass support frame 20 is conventional except for quick release hinges.

FIG. 6 shows a side view of one embodiment of an actuated knee 11 coupled to the thigh frame 3 (FIG. 1) and the shank frame 2 (FIG. 1). The actuated knee 11 includes a thigh clutch assembly, a spring clutch assembly, a transfer arbor assembly, and a torsion spring 70. The thigh clutch assembly includes a thigh clutch wire 73 (at output arbor of the thigh clutch) and a thigh clutch actuator 75. The thigh clutch assembly is a mechanism for transferring torque from the thigh frame 3 (FIG. 1) to the transfer arbor under microprocessor control. The spring clutch assembly includes a spring clutch wire 74 (at output arbor of the spring clutch) and a spring clutch actuator 76. The spring clutch assembly is a mechanism for transferring torque from one arm of the torsion spring to its other arm under microprocessor control. The transfer arbor assembly includes two side plates (not shown), a thigh clutch arbor 71 (at input arbor of the thigh clutch), a spring clutch arbor 72 (at input arbor of the spring clutch), and a transfer arbor pin 83. Knee axle 84 provides a means for the shank frame 2, thigh frame 3, and the transfer arbor to rotate around a single axis of rotation.

The thigh frame 3 includes a thigh frame side strut 77, a thigh frame side plate 78, and a thigh wire termination 79 that are fixed relative to one another. The shank frame 2 includes a shank frame side strut 80, a shank frame side plate 81, a torsion arm pin 82 that and are fixed relative to one another. One arm of the torsion spring is directly coupled to the shank frame 2 (FIG. 1) via the torsion arm pin 82 while the other arm of the torsion spring 70 is directly coupled to the thigh clutch arbor 71 via transfer arbor pin 83. The thigh frame 3, the shank frame 2, and the transfer arbor all rotate around a common axis of rotation. Stops prevent hyper extension of the knee joint and limit flexion of the knee to approximately 130 degrees.

FIG. 7 shows a perspective view of a transfer arbor assembly of the actuated knee 11 of FIG. 6. The transfer arbor includes a pair of transfer arbor side plates 90 (one shown), a thigh clutch arbor 71, a spring clutch arbor 72, and a transfer arbor pin 83. The transfer arbor side plates 90 couple the thigh clutch arbor 71, the spring clutch arbor 72, and the transfer arbor pin 83. In a preferred embodiment, a thin steel thigh clutch sleeve 91 is heat shrunk on an outer surface of the thigh clutch arbor 71 to form a thigh clutch face. Similarly, a thin steel spring clutch sleeve 85 is heat shrunk on an outer surface of the spring clutch arbor 72 to form a spring clutch face. The outer surfaces of the thigh clutch arbor 71 and spring clutch arbor 72 are circular with a center coincident with a knee axle 84. To create an arbitrary hyper linear spring, the inner surface of the thigh clutch arbor is not circular.

The transfer arbor assembly is shown with the torsion spring 70 at a knee angle of zero degrees. With the thigh clutch activated, the thigh frame 3 is coupled to the thigh clutch arbor 71. Accordingly, any knee flexion causes the thigh clutch arbor 71 to rotate counter clockwise around the knee axle 84. A torsion arm pin 82 provides a means for pinning one arm of the torsion spring 70 to a shank frame 2. The transfer arbor sideplate cutout 92 (FIG. 8A), allows the transfer arbor assembly to rotate counter clockwise around the knee axle 84 approximately 1.1 radian. A transfer arbor pin 83 provides a means for pinning the other end of the torsion spring 70 to the thigh clutch arbor 71.

FIGS. 8A-8C show the torsion spring 70 relationship with the thigh clutch arbor 71 and shank frame 2 (FIG. 1) at three different knee angles. FIG. 8A shows a side view of the transfer arbor assembly with the torsion spring 70 at a zero knee angle. The shape of torsion spring 70 and the inner surface contour of thigh clutch arbor 71 are engineered to achieve the non-linear hardening back torque versus knee angle function desired. While non-trivial to design, well known techniques can be employed to achieve almost any monotonic torque function. Many torque functions can be realized without contouring the inner surface of the thigh clutch arbor 71. As a general rule, hyper linear behavior is gained by providing continuous stops that reduce the length of steel allowed to sustain torsion. At a knee angle of zero, the entire length of the torsion spring is allowed to sustain torsion. FIG. 8B shows the torsion spring 70 sustaining torsion of 24 degrees. As can be seen, only about 70% of the spring length is allowed to sustain torsion since the remaining 30% is fixed to the inner surface of the thigh clutch arbor 71. FIG. 8C shows maximum spring where 100% of the spring length is in contact with the inner surface of the thigh clutch arbor 71. This knee angle is called the torsion spring angle limit. Knee flexion greater than the torsion spring angle limit is possible because the thigh clutch will allow slipping once its maximum torque limit is reached. The torsion spring 70 is cut from spring steel blank with a shape dictated by the non-linear hardening spring function desired.

In one embodiment, both a microprocessor activated thigh clutch and spring clutch are used during normal operation. Both clutches are variants of a class of clutches called one-way dual-state clutches. In all clutches, there is an input arbor and an output arbor and a means for coupling torque between input arbor and output arbor. In dual-state clutches, there are two states that can be called released and actuated. In its released state, negligible torque can be transferred from input arbor to output arbor before slippage occurs. In the actuated state, a large torque can be coupled from input arbor to output arbor before slippage occurs. Transition between states is affected either mechanically or electrically typically via a solenoid.

Operation of a one-way dual-state clutch (employed in an embodiment of the invention) is identical to a dual-state clutch in the released state. In the actuated state, operation of the one-way dual-state clutch differs because large amounts of torque can be transferred from input arbor to output arbor only in one rotational direction. This torque transfer direction is called the 'hard direction'. When in the actuated state, only a small amount of torque can be transferred from input arbor to output arbor before slippage occurs in the other direction, called the 'easy direction'. Note that in any physical implementation of a one-way dual-state clutch, the maximum torque transferable between the input arbor and the output arbor without slippage is limited by the physical parameters of the clutch. Moreover, easy direction torque will normally be much larger than release state transfer torque.

FIG. 9 shows a perspective view of one embodiment of a spring clutch of the present invention. Preferably, the spring clutch is a one-way dual-state clutch called a spring wrap clutch. The spring wrap clutch includes multiple turns of music wire 100 coiled around the spring clutch arbor 72. Spring clutch arbor 72 is fixed to transfer arbor 71 via transfer arbor sideplates 90. The coiled music wire 100 preferably has an inside diameter of about 0.5 millimeters larger than the spring clutch arbor 72 outside diameter. The termination end 101 of the music wire 100 is looped around a torsion arm pin 82 and secured by crimping a wire oval 102 as shown. A control end 103 of the music wire 100 is formed as shown allowing the control end 103 to exit the transfer arbor sideplate 90 through transfer arbor sideplate cutout 92. The control end 103 is also formed to allow a spring clutch control arm 104 to hinge at the control end 103 of music wire 100.

The spring wrap clutch utilizes the well known capstan effect. Activation and release state are controlled by the application of a control force $F_c$ 105 applied to the control end 103 of the coiled music wire 100 via the spring clutch control arm 104. With zero $F_c$, the music wire 100 assumes an unstressed inside diameter slightly larger than the outside diameter of the spring clutch arbor 72. In this state, virtually no torque can be transferred between the shank frame 2 and the transfer arbor 71. As control force $F_c$ 105 increases, the inner diameter of the music wire 100 decreases. When the force $F_c$ 105 reaches a critical value called the activation force $F_a$ (preferably approximately 1.7 newtons), all coils of the music wire 100 are in contact with the outer surface of the spring clutch arbor 72. When $F_c$ is greater than $F_a$, the difference is available to create a much larger holding force $F_h$ 106 at the termination end 101 of the music wire 100. The ratio of the holding force $F_h$ 106 to available control force ($F_c-F_a$) varies as the well known capstan effect formula:

$$\mathrm{Exp}[N\partial],$$

where N is the number of wire turns (in radians) making contact with the spring clutch arbor 72 outside surface; and $\partial$ is the coefficient of friction between music wire 100 and spring clutch arbor 72 outside surface.

In a capstan effect system, the peak force occurs at the termination end 101 and decreases exponentially. Accordingly, an implementer sizes the diameter of the music wire 100 based on the peak force. Assuming 150 newton meter maximum torsion spring 70 torque, a music wire 100 having a diameter of 2.311 millimeters is required to sustain the 3750 newton peak force in the wire. With this minimum wire diameter limitation, only 5.75 turns of 2.311 millimeter music wire will fit on the surface of spring clutch arbor 72. Assuming a control force 105 $F_c$=6 newtons and a coefficient of friction of $\partial$=0.18 yields a 4000 newton maximum holding force $F_h$ 106.

To efficiently generate the control force $F_c$ 105, an extension spring is used to couple the end of spring clutch control arm 104 and an actuator. The actuator is composed of a geared motor driving a CAM to rotate the activation arm. The CAM makes one full turn per step and utilizes a surface contour that allows very fast transition from the activated to the released states. The CAM contour is also engineered for constant battery current drain when transitioning between states; and no battery current drain after reaching either state.

The amount of power consumption is directly proportional to the tolerances that can be engineered. To allow for ageing and manufacturing tolerances, an extension spring length change of 4 millimeters is assumed. The amount of energy needed to extend an extension is 0.5 $\Delta x\ F_{max}$, where $\Delta x$ is the extension distance in meters and $F_{max}$ is the maximum force in newtons. Assuming a geared motor/CAM efficiency of 50% implies that 0.024 joules of energy will be drained from the battery for each step.

FIGS. 10A-10C show elements of a spring clutch activator in its partially activated state; it's fully activated state, and its released state. A direct current (DC) motor 110, with a pinion gear 111, drives a first stage compound gear 112 rotating on first stage gear axle 113. The first stage compound gear 112 drives a second stage compound gear 114 rotating on second stage gear axle 115. Finally, the second stage compound gear 114 drives a third stage simplex gear 116 rotating on CAM axle 117. A control CAM 118 is fixed to a gear axle 117 and drives a actuation roller 122. The overall gear ratio between motor and control CAM 118 is selected such that CAM can rotate one turn in 160 milliseconds. An actuation arm 120 pivots on an actuation arm axle 121. To allow only one activation mechanism per actuated knee pair, the actuation arm 120 is bent from a single aluminum rectangular with two activation arm axles 121, one for the inner actuated knee and one for the outer actuated knee. The single actuation roller 122 rides along the control CAM 118 causing the actuation arm 120 to rotate around the actuation axle 121. Finally, an actuation spring 123 couples the actuation arm 120 and a clutch control arm 104. The control CAM 118 normally rotates counter clockwise and is shown midway between released and activated states. FIG. 10B shows the spring clutch activator in its released state while FIG. 10C shows the spring clutch activator in its activated state. In the activated state, the control CAM 118 contour is engineered to prevent control force $F_c$ 105 from back driving the motor.

FIG. 11 shows a side view of a thigh clutch according to the principles of the present invention. The thigh clutch couples torque from the thigh frame 3 (FIG. 1) to the transfer arbor 71 (FIGS. 6-8). It must transition from its activated state to its release state in a few milliseconds or a wearer will sense knee binding following toe off. When in the released state, the thigh frame 3 and transfer arbor 71 must rotate freely relative to one another or the wearer will have difficulty flexing his knee. When activated, the wearer should experience only a small back torque when attempting to extend his knee. When activated, a microprocessor must be able to finely control the amount of torque transferred from thigh frame 3 to transfer arbor 71 to affect controlled slippage. This implies that the thigh clutch must dissipate energy. Since the thigh clutch is positioned on the outer surface of the transfer arbor 71, it must prevent contamination of the surface by environmental agents that could significantly change the clutch surface's coefficient of friction. Lastly, like the spring clutch, it must go through one activation/release cycle per step. Thus, the amount of battery power consumed per step must be small.

The thigh clutch includes preferably five identical clutch shoes 130, one end clutch shoe 131, a first turn wire 132, a last wire turns 133, and the thigh clutch actuator 75. Each of the six clutch shoes 130/131 slides in the channel formed by the outer surface of the thigh clutch arbor 71 and transfer arbor sideplates 90 (FIGS. 6-8). The first turn wire 132, is fixed to the thigh frame 3 (FIG. 1) via a thigh wire termination 79. The first turn wire 132 is then routed clockwise through channels in each of the five clutch shoes 130 and half way through a channel in end clutch shoe 131. The first turn wire 132 then wraps ½ turn around first turn termination post 134 and then is routed counter clockwise through a second channel in each of the clutch shoes 130/131. Finally, the first turn wire 132 is fixed to the thigh frame 3 via the thigh wire termination 79. Two screws on each clutch shoe 130/131 fix the first turn wire 132 to each clutch shoe 130/131 to prevent their slippage relative to the first turn wire 132. All routing of the first turn wire 132 occurs in channels on the outside of the clutch shoes 130/131. The last wire turns 133 is looped around a first turn termination post 134 and fixed with a crimped oval sleeve 102. The last wire turns 133 is then routed through a channel in the end clutch shoe 131 until it reaches the surface of thigh clutch arbor 71. The last wire turns 133 is then routed clockwise through an inner surface channel in each clutch shoe 130/131, for 2.75 wraps. Lastly, the last wire turns 133 emerges from the surface of thigh clutch arbor 71 through a channel in the clutch shoe 130 and terminates in the thigh clutch actuator 75. It should be obvious that the disclosed thigh clutch is yet another application of the capstan effect with a total of 3.75 turns.

There are numerous benefits to utilizing a two stage scheme in the thigh clutch. The first benefit is that it allows a clutch material to be employed which is specifically designed for controlled slippage and power dissipation. Secondly, the clutch shoes 130/131 reduce the peak pressure between the first turn wire 132 and thigh clutch arbor 71 by an order of magnitude compared to a scheme not employing clutch shoes. Thirdly, it allows the last wire turns 134 to be much smaller than would be needed in a single wire scheme. Fourthly, it provides a means for protecting the outer surface of the transfer arbor from contaminants. Lastly, it provide a means for solving the free rotation problem when the thigh clutch is in the release state.

FIG. 12 shows a perspective view of a clutch shoe 130 of FIG. 11. The clutch shoe 130 includes a plastic or aluminum clutch shoe frame 140 having two first turn channels 141 used to route the first turn wire 132. Clutch pads 142 are bonded to the bottom surface of clutch shoe 140 forming an interior channel 143 in which the last wire turns 133 is routed. The interior surface of the interior channel 143 is covered with a Teflon tape to reduce the coefficient of friction between the upper surface of the last wire turns 133 and the inside surface of the interior channel 143. The Teflon tape enables the last wire turns 133 to freely unwrap while touching the bottom surface of the interior channel 143

The first turn wire 132 is formed to have an inside diameter larger than the diameter of the first turn channels 141. When the first turn wire 132 is assembled with the clutch shoes 130/131 and terminated at the thigh wire termination 79, the assembly will naturally uncoil, but is prevented from uncoiled more than a fixed amount by a first turn uncoil stop 145 as shown in FIG. 11. When the control force $F_c$ is reduced to zero, the last wire turns 133 will naturally unwrap until it touches the Teflon tape on the interior channel 143 over its entire length. When this unwrapping reaches the first turn termination post 134, all clutch shoes 130/131, will lift off the surface a controlled amount limited by a first turn uncoil stop 145. In this state, none the last wire turns 133 are touching the outer surface of thigh clutch arbor 71 (FIGS. 6-8). Accordingly, virtually no torque can be transferred from thigh frame 3 (FIG. 1) to thigh clutch arbor 71 during knee flexion nor during knee extension.

As the control CAM 118 (FIG. 10) rotates to a position of maximum control force $F_c$ 105, the last wire turns 133 wraps tightly around the outer surface of thigh clutch arbor 71. The force applied by the last wire turns 133 at the first turn termination post 134, is insufficient to cause the set of clutch shoes 130/131 to wrap tightly against the outer surface of thigh clutch arbor 71. This does not create a problem in operation however because as soon as flexion knee torque is created at heel strike, the ensemble of clutch shoes 130/131, immediately tightly wraps on the outer surface of thigh clutch arbor 71. This effect (not present in a conventional wrap spring clutch) results in the thigh frame 3 slipping in the hard direction for about one degree before it 'catches' and transfers arbitrary torque to the thigh frame. This undesired affect is not a problem however in normal operation of the brace.

Operation of the thigh clutch actuator 75 is almost identical to that of the spring clutch actuator 76. There are three differences. First, instead of the actuation spring 123 driving the spring clutch control arm 104, the actuation spring 123 drives the end of last wire turns 133 through a spring clutch control arm equivalent, which allows adjustment for clutch shoe wear. Second, it is desired that the activation force is adjustable by the microprocessor to allow controlled descent.

To enable a 150 newton meter torque to be transferred between thigh frame 3 and thigh clutch arbor 71, a 2400 newton force must be supported in the first turn wire 132. This force exponentially decreases along the first turn wire 132 reaching a minimum at termination post 134 of 2400 Exp[−5.64 $\partial_1$] where $\partial_1$ is the coefficient of friction between the clutch pads 142 and the thigh clutch sleeve 91. This coefficient of friction is strictly dependent of clutch pad 142 material selected but is preferably in the 0.35-0.45 range. Using the smaller number, the peak force in the last wire turns 133 at the first turn termination post 134 is approximately 333 newtons. With the smaller peak force requirement, 1.15 millimeter music wire can be employed in last wire turns 142. Assuming a coefficient of friction of 0.18 for music wire on the steel sleeve covering the thigh clutch arbor 71 results in a holding force requirement to the thigh clutch actuator 75 of less than 15 newtons.

To achieve a controllable activation force, the drive electronics for the thigh clutch actuator is allowed to drive the control CAM 118 in both rotation directions. In descent walking, the microprocessor does not transition from the released state to the activated state as fast as possible. Rather, it regulates the control CAM 118 rotation angle to achieve a controlled descent. By allowing the control CAM 118 rotation in both directions, underestimation of the slippage torque is compensated by backing off the control CAM 118 angle.

A preferred embodiment of the invention utilizes a microprocessor to regulate transitions between released and activated states in the spring clutch and thigh clutch actuators. These transitions must occur at specific times in the gate cycle. An embodiment of the present invention utilizes several conventional mechanisms to monitor the state of the brace. Conductive plastic continuous potentiometers are employed to monitor the control CAM 118 angular rotations in both clutch actuators. Theses sensors provide a voltage proportional to the control CAM 118 angle over a 340 degree angle of rotation and produce zero voltage for the remaining 20 degrees of rotation. In a preferred embodiment, the 20 degree sector is aligned such that it begins at control CAM 118 contour position where it rapidly decreases its radius. Two conventional conductive plastic potentiometers, augmented with a torsion spring return mechanism are employed to monitor the angle between the shank frame 2 and both the shoe frame 1 and thigh frame 3 (FIG. 1). A conventional dual axis MEMS accelerometer is employed to monitor the orientation of the shank frame relative to the earth's gravitational field.

FIG. 13 shows a sensorized insole for use in a wear's shoe. The sensorized insole includes a heel pressure pad 150, a little toe pressure pad 151, and a big toe pressure pad 152 that provide a means for monitoring the pressure applied by the wearer's foot against the shoe insole. Each pressure pad consists of three layers of copper foil interlaced with two foam dielectric layers. This structure forms a capacitor whose capacitance varies inversely with the separation distance between outer foil layers. A square wave, produced by the electronics module, drives a common lead of each of the three pressure pad capacitors. The non-common lead of each of the three pressure pads is routed to three pressure pad preamplifiers 153. These preamplifiers amplifies the capacitance outputs and change their impedance levels. The amplified signals are then routed to an electronics module via an insole cable 154.

The two pressure pads 151/152 in the toe area allow sensing command signals from the wearer by detecting the sequence and duration of pressure applied to the pads. This allows the wearer to give toe activated commands to the brace when explicit control is allowed. The pads 151/152 also allow training the microprocessor to associate wearer defined pad pressure sequences to the available commands. The pressure pad sensors are quasi linear in that the microprocessor can easily detect the difference between non, light, moderate and heavy pressure application to each pad. Use of these type of pressure measuring sensors is favored over conventional force sensors because they are inexpensive and the sensitivity can be selected by proper choice of the foam dielectric.

Figure 14:
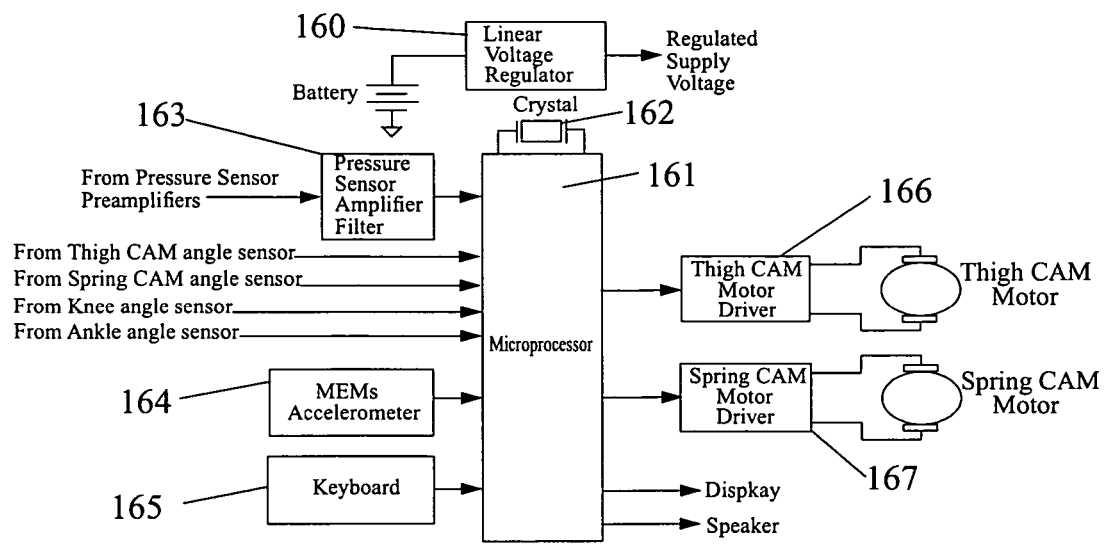
FIG. 14 is a block diagram of an electronics control module.

FIG. 14 is a block diagram of an electronics control module. The electronics and motor control circuits are preferably powered from three AA batteries connected in series. The battery output voltage is regulated down to 3.0 volts via voltage regulator 160. All behavior of the brace is effected by a program resident within an 8-bit microprocessor 161. Timing of all events is derived from the microprocessor's oscillator whose frequency is regulated by a crystal 162. The output voltages of four potentiometers are routed directly to A-D inputs of the microprocessor 161. The signals produced by the three pressure pad preamplifiers 150 (FIG. 13), are amplified, rectified and filtered in pressure pad amplifier/filters 163. A dual axis accelerometer 164 allows measurement of the acceleration on the shank frame 2 (FIG. 1) over a +/−1.5 G acceleration range to one part in 1000. The accelerometer is employed both to detect heel strike and to sense the shank frame 2 orientation relative to the earth's gravitational field. A keyboard 165 allows the wearer to manually key in commands to the electronics module during configuration. Note that wearer to electronics commands are issued infrequently and a preferred method utilizes sequences of pressures applied to the pressure pads in the sensorized insole.

A pulse width modulated (PWM) current limited thigh motor driver 166 is employed to drive the motor within the thigh clutch actuator 75. The driver provides a means for the microprocessor to drive the motor in both directions. A PWM current limited spring motor driver 167 is employed to drive the motor within the spring clutch actuator 76. The microprocessor 161 also drives two LEDs, a LCD display, and a speaker. Note that the keyboard 165, display and LEDs are used for configuration of the brace and do not play a role during normal operation.

Except for the MEMs accelerometer that is interrupt driven, all activities of the microprocessor occur in the main loop, executed 200 times per second. Regardless of system control state, the microprocessor 161 first gathers values from each of the sensors and then makes a determination of whether to change state or not. It then executes the function associated with the current state. For the majority of main loop executions, the function executed is null, i.e., no action is indicated. Generation of the microprocessor code is straightforward for any practitioner in the field of real time processing employing feedback control.

Figure 15:
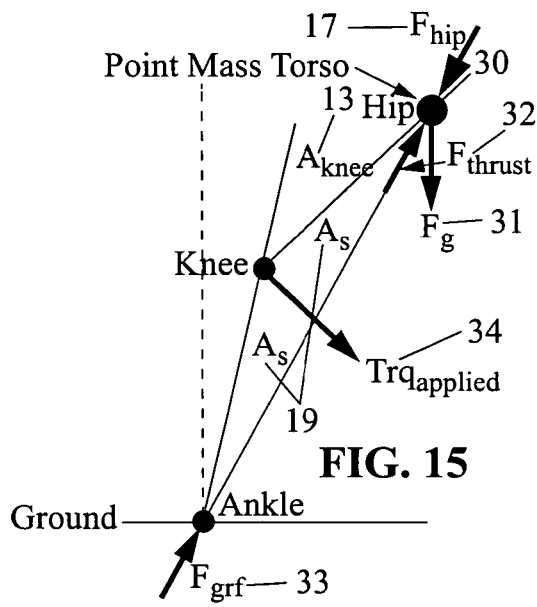
FIG. 15 shows geometry, forces and torques in a simplified model having a massless leg and a point mass torso.

FIG. 15 shows the geometry and forces in a model used to show how an embodiment of the present invention reduces the incidence of falls caused by inadequate wearer femur/tibia torque. It is assumed that a torso mass 30 is concentrated at the hip. This mass creates a force $F_{hip}$ 17 applied to the hip socket of the support leg. $F_{hip}$ 17 is the sum of the gravitational force $F_g$ 31 and inertial forces. Since the sum of the forces applied to the hip socket must equal zero, the leg thrust force $F_{thrust}$ 32 equals $-F_{hip}$. Assuming massless legs and brace with no ankle torque, ground reaction force $F_{grf}$ 33 exactly equals $F_{thrust}$ 32.

The application of a $F_{hip}$ 17 and $F_{grf}$ 33 to the braced leg results in a torque $Trq_{applied}$ 34 being applied to the brace shank and thigh frames. It is straightforward to compute that $Trq_{applied}=F_{hip}$ Length$_{femur}$ Sin$[A_s]$, where Length$_{femur}$ is the length of the femur connecting hip socket and knee. At each instant of time, $Trq_{applied}$ must equal the sum of the torque generated by the brace plus the knee torque generated by the wearer's quadricep muscles. Assuming Sin$[x]=x$ and $A_{knee}=2 A_s$, $Trq_{applied}=2 F_{hip}$ Length$_{femur} A_{knee}$. Clearly, $F_{hip}$ 17 must be greater than or equal to the torso weight since it is the vector sum of the gravitational and inertial forces. This implies that $Trq_{applied}$ 34 is greater than the torso weight times the knee angle $A_{knee}$ 13. Thus, if the knee angle increases by 10%, the sum of the brace torque plus the wearer generated knee torque must increase by 10%.

Figure 16:
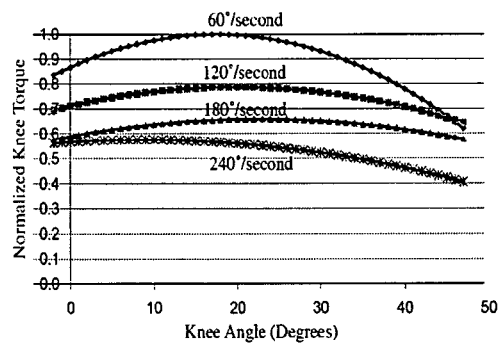
FIG. 16 shows measurements of maximum knee torque of a human versus knee angle at four different knee angular velocities.

FIG. 16 shows measurements of maximum knee torque versus knee angle at four different knee angular velocities. The first observation is that the maximum knee torque peaks at approximately $A_{knee}=20$ degrees and then rapidly decreases. At high angular knee velocity, maximum knee torque decreases by almost a factor of two. Since the knee torque does not increase proportionately to knee angle, there exists a critical knee angle $A_{crit}$ for humans where the amount of torque which can be generated equals $Trq_{applied}$ 34. Since $F_{hip}$ 17 is the sum of the gravitational and inertial forces, humans select their gait to prevent ever exceeding $A_{crit}$. If a human ever exceeds this critical knee angle, positive feedback will occur; the leg will no longer be able to generate the needed thrust, and the human falls.

To provide torso support at any knee angle and especially at higher gait speeds, an embodiment of the invention utilizes a torsion spring which is a member of a class of well known torsion springs called non-linear hardening torsion springs. This spring is one part of the brace knee joint 11 (FIG. 1). In a linear torsion spring, the back torque generated by the spring in response to rotating one arm of the spring relative to the other increases directly proportionally to the rotation angle. In a non-linear hardening torsion spring, the back torque increases faster than the rotation angle. Thus for example, in a non-linear hardening torsion spring, the relationship between torque and angle could be $Trq_{knee}=K_1 A_{knee} (1+K_2 A_{knee}^S)$ where $A_{knee}$ is the knee angle and $K_1$, $K_2$ and $S$ are engineered parameters.

Figure 17A:
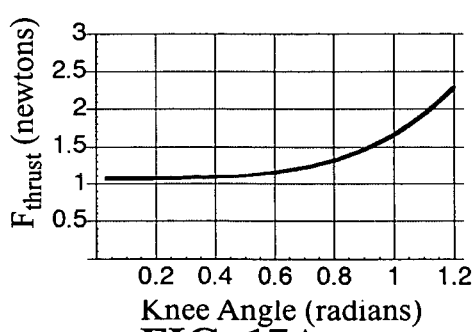
FIG. 17A shows the leg thrust produced at the hip sockets of a wearer of the invention of FIG. 1 versus knee angle for one variant of torsion spring.

FIG. 17a shows the leg thrust produced at the hip sockets of a wearer of the invention of FIG. 1 versus knee angle $A_{knee}$ 13 for one variant of a non-linear hardening torsion spring. As seen, the magnitude of the braced leg thrust actually increases as the knee angle increases. If the zero knee angle $F_{thrust}$ 32, is chosen to be approximately 1.25 body weight, then the maximum thrust is approximately 275% of body weight at maximum knee angle. This increase in leg thrust with knee angle is extremely desirable for wearer's of the brace while running because the inertial force component of $F_{hip}$ 17 becomes greater than the gravitational component. It should be recognized that embodiments employing different positive values of $K_2$ and $S$ will all yield the benefits of increasing thrust with knee angle.

In addition to the basic torso support benefit, an embodiment of the invention also reduces the metabolic energy consumption normally needed for walking or running. Measurements of metabolic energy consumption in humans show a quadratic increase in metabolic energy consumption for low average velocities and a cubic increase at higher velocities. Measurements of the GRF show a substantial increase in peak $F_{hip}$ 17 at high velocities. For example, an olympic class sprinter must generate a leg thrust approximately equal to 500% of body weight and do so at the highest rate of angular knee velocity.

Figure 18:
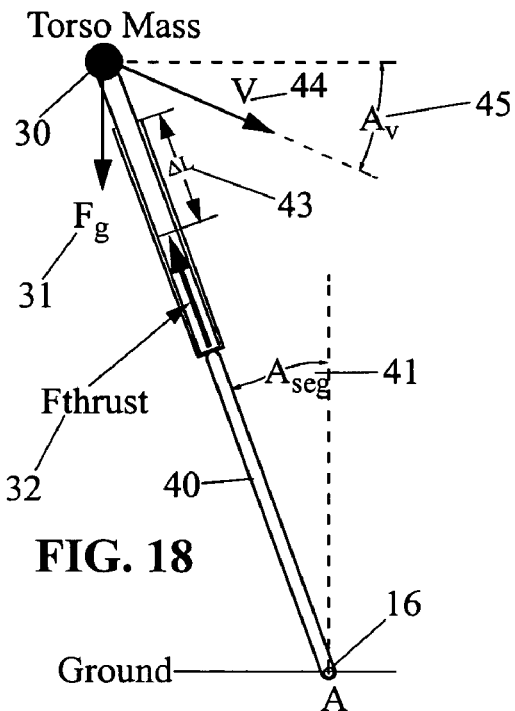
FIG. 18 shows angles, forces, and velocity definitions of a Seg model.

FIG. 18 shows angles, forces, and velocity definitions of a simple model used to illustrate the interchange between kinetic, potential and knee spring energy during walking and running. In the model, the brace's shoe, shank, thigh frames are collapsed into a massless support leg mechanism called a Seg 40. The entire torso plus swing leg is collapsed down to a point torso mass 30. The telescoping Seg 40 structure constrains the torso mass to slide only along its axis. One end of the Seg 40 rotates around ankle joint 16 while the other end of the Seg 40 is pinned to torso mass 30. The Seg angle $A_{seg}$ 41 is the angle between the Seg 40 axis and the gravitational vector. A positive Seg angle $A_{seg}$ 41 angle indicates that ankle is ahead of the hip. At heelstrike Seg angle $A_{seg}$ 41 is always positive. The model is walking/running from left to right. The Seg 40 produces a force $F_{thrust}$ 32 on the torso mass 30 in a direction colinear with its axis. Accordingly, the $F_{thrust}$ 32 has a direction colinear with the line joining ankle and hip socket. If $L_0$ is the distance between hip and ankle at heelstrike with the knee fully extended, the magnitude of the force $F_{thrust}$ 32 is strictly dependent on the difference ($\Delta L$ 43) in the distance from hip to ankle from $L_0$. $F_{thrust}$ 32 is zero when $\Delta L$ 43 is greater than zero because the distance between hip and point on the ground representing the ankle is greater than the fully extended leg length. $F_{thrust}$ 32 is non-zero when $\Delta L$ is less than or equal to zero because the action of the torsion spring in the brace produces a force $F_{thrust}$ 32 as described above. The force $F_{thrust}$ 32 satisfies the equations:

$$\Delta L = 2L_0(1-\cos[A_s]);$$

$$Trq_{knee}[2A_s]=F_{thrust}\text{Length}_{femur} \sin[A_s];$$

where, $Trq_{knee[\ ]}$ equals the torque produced by the torsion spring in the brace's knee joint as a function of knee angle (i.e. twice $A_s$). It is modeled as a polynomial of the form $Trq_{knee}=K_1 A_{knee}(1+K_2 A_{knee}^S)$.

In the dynamic analysis, each step starts at heelstrike with the Seg 40 having a positive Seg angle $A_{seg}$ 41. The torso mass 30 is assumed to have velocity vector V 44 at heelstrike. That is, the torso is assumed to be moving from left to right with downward angle $A_v$ 45 at heelstrike. The Seg 40 is assumed to make a Seg angle $A_{seg0}$ 41 relative to vertical at heelstrike. The gravitational force $F_g$ 31 is applied at all times. The brace thrust force $F_{thrust}$ 32 is applied to the mass only when $\Delta L$ 43 is non-positive. At heelstrike, it is assumed that $\Delta L=0$, $A_{seg}$ 41 has some positive value $A_{seg0}$, and the torso velocity vector ΔL 44 makes a positive angle of $A_{v0}$ 45 with ground. To show typical behavior, a knee spring is simulated with $K_1=0.2$, $K_2=0.49$ and $S=4$.

Figure 17B:
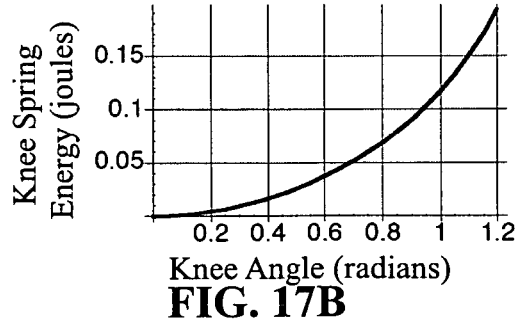
FIG. 17B shows the torsion spring energy versus knee angle relationship of the invention of FIG. 1 versus knee angle for one variant of torsion spring.

FIG. 17A shows the $F_{thrust}$ 32 force versus knee angle relationship of the Seg model shown in FIG. 18 applied to a mass having a weight of one newton as a function of knee angle $A_{knee}$ 13. FIG. 17B shows torsion spring energy versus knee angle relationship of the Seg model of FIG. 18. Note that for a wearer having a weight of 800 newtons, the torsion spring must be designed to store 152 joules and generate a torque of about 300 newton meters at maximum knee angle.

A step starts with the new support leg heel just touching ground. At this instant, called heelstrike, the wearer of the brace has selected three gait parameters $A_{seg0}$ 41, $V_0$ 44 and $A_{v0}$ 45 to define all aspects of the gait during each step. A stable gait cycle is defined as one where the three gait parameters are the same at the start of each step. As is well known, without some time dependent control of the torsion spring, the wearer can only independently select two of the three gait parameters. That is, for a particular choice of $V_0$ and $A_{v0}$, there exists one and only one $A_{seg0}$ which results in a stable gait cycle. If the wearer does not select the particular value of $A_{seg0}$ associated with the initial selection of $V_0$ and $A_{v0}$. the torso velocity V 44 at the end of the step will not be the same as at the beginning of the step.

It can be shown that the necessary and sufficient condition for a stable gait cycle to occur is that the knee spring reach its maximum torsion at exactly the time that the Seg 40 is vertical i.e. $A_{seg}=0$. If the brace wearer can choose a set of three gait parameters which results in maximum torsion at $A_{seg}=0$, he will gain the benefits of reduced energy consumption with a stable gait cycle. Experience has shown that while this is possible for humans to achieve a stable gait cycle, it is problematic. In particular, it requires a lengthy adjustment period and creates stability problems when the wearer changes average gait speed.

To allow independent selection of all three gait parameters, a preferred embodiment of the invention includes a mechanism which causes the knee angle to be frozen at $A_{segc}$ when maximum knee torque is sensed on the knee spring. The knee angle is unfrozen (i.e. releasing the energy stored in the knee spring back into the system) when $A_{seg}=-A_{segc}$. This mechanism produces a stable gait cycle regardless of the values chosen provided that $A_{segc}$ is positive.

Figure 20A:
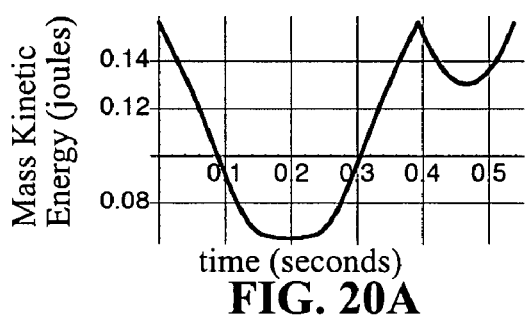
FIG. 20A shows the normalized torso kinetic energy versus time.
Figure 20B:
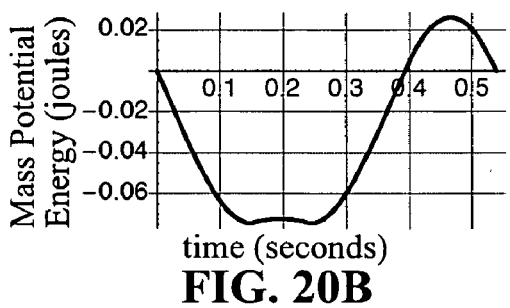
FIG. 20B shows the normalized torso potential energy versus time.
Figure 20C:
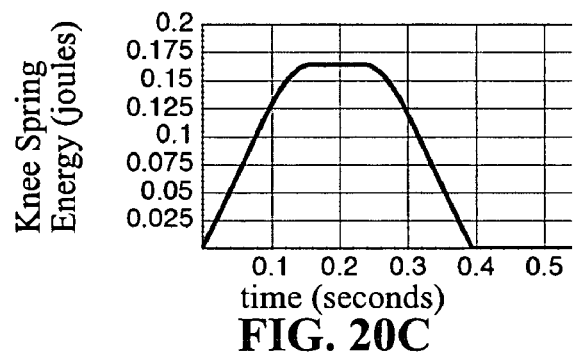
FIG. 20C shows the normalized knee spring energy versus time.
Figure 21:
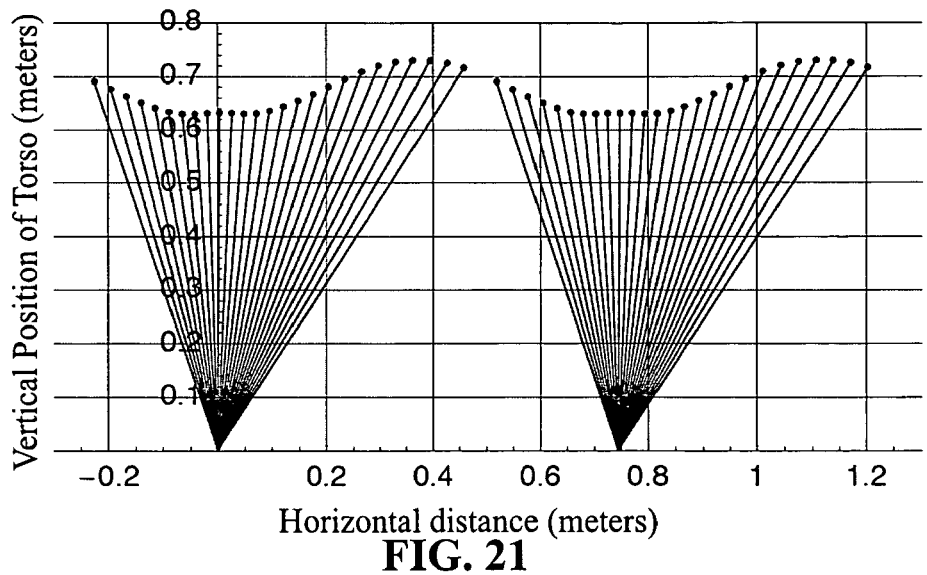
FIG. 21 shows the position of the torso and the Seg at 20 millisecond intervals over two successive steps.

FIGS. 19-21 show the results of a simulation of the simplified model of FIG. 18 with $A_{seg0}=20$ degrees and horizontal/vertical components of the torso velocity equal to 1.6/−0.712 meters/second and a torso mass 30 weight of one newton. FIG. 19A shows the Seg angle versus time during one step of a simulation model walking at 1.38 meters/second over level ground. FIG. 19B shows the Seg thrust versus time during one step of a simulation model walking at 1.38 meters/second over level ground. From heelstrike to about 0.157 seconds, kinetic and potential energy of the torso mass is transferred to the knee spring. At 0.157 seconds ($A_{seg}=4.12°$) the spring clutch freezes the knee spring angle and the microprocessor remembers that $A_{segc}=4.12°$. As a result of freezing the knee spring, $F_{thrust}$ 32 immediately drops to that value required by a mass rotating losslessly around the ankle at constant distance from the ankle. Note that during this period when the knee spring is frozen, $F_{thrust}$ 32 is less than torso mass 30 weight. At 0.23 seconds, the microprocessor senses that $A_{seg}=-A_{segc}$ and transitions the spring clutch to its released state. This release immediately causes $F_{thrust}$ 32 to increase to the same value it was at the time that $A_{seg}=A_{segc}$. After release, the mass is thrust upward and forward until the knee angle reaches zero at 0.385 seconds. At that point in time ΔL becomes positive resulting in $F_{thrust}$ 32 dropping to zero.

Figure 19A:
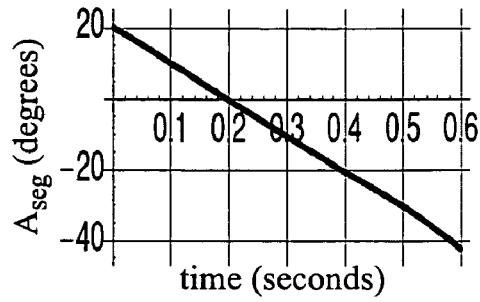
FIG. 19A shows the Seg angle versus time during one step of a simulation model walking at 1.38 meters/second over level ground.
Figure 19B:
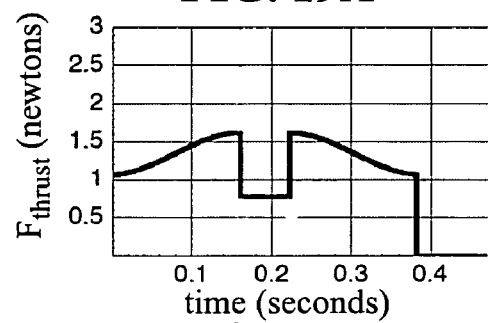
FIG. 19B shows the Seg thrust versus time during one step of a simulation model walking at 1.38 meters/second over level ground.
Figure 19C:
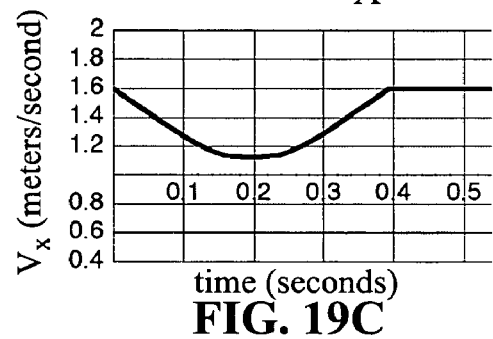
FIG. 19C shows the horizontal component of the torso velocity versus time during one step of a simulation model walking at 1.38 meters/second over level ground.
Figure 19D:
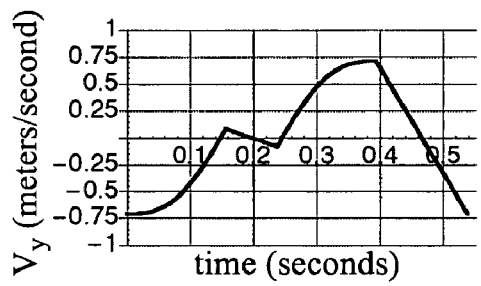
FIG. 19D shows the vertical component of the torso velocity versus time during one step of a simulation model walking at 1.38 meters/second over level ground.

FIG. 19C shows the horizontal component of the torso velocity versus time during one step of a simulation model walking at 1.38 meters/second over level ground, FIG. 19D shows the vertical component of the torso velocity versus time during one step of a simulation model walking at 1.38 meters/second over level ground; As seen, at the end of the support epoch (at approximately 0.385 seconds) the horizontal component of torso velocity is exactly the same as it was at heelstrike. The vertical velocity component, however, is the exact negative of its value at heelstrike. In essence, the mass has losslessly rebounded off the ground like a perfectly inelastic ball. Since the only force on the mass following the support epoch is gravity, the vertical component of the torso velocity will linearly decrease until it reaches the right leg heelstrike initial condition.

While the sum of kinetic, potential and knee spring energy must be constant at each instant of time during the step cycle, energy is constantly being transferred between them. FIGS. 20A-20C show the kinetic, potential, and knee spring energy versus time over one step interval. As expected, the knee spring energy increases almost linearly until time 0.157 seconds at which time the spring clutch freezes the knee angle. This results in the energy stored in the knee spring remain constant until its release at 0.23 seconds. The energy stored in the knee spring then decreases almost linearly until it reaches zero at 0.385 seconds.

FIG. 21 shows the spatial position of the Seg and torso mass at 20 millisecond time intervals for a sequence of left step followed by right step.

Most human walking/running occurs over level terrain. However, if wearing the brace prevents walking over uneven terrain, the brace becomes impractical. For example, powered wheelchairs allow comfortable support of the torso weight via the hip sockets with virtually no metabolic energy consumption at high forward speeds. Their primary deficiency lies in problems associated with navigating uneven terrain, especially stairs.

The uneven terrain problem can be partitioned into ascent and descent. In ascent, the new support leg ankle height is higher than the old support leg ankle height. In descent, the new support leg ankle height is lower than the old support leg ankle height. In ascent, the wearer must increase system energy on each step by the product of body weight (in newtons) and step height differential (in meters). No passive brace such as discussed in an embodiment of the invention will supply that energy; it must be supplied from the metabolism of the wearer. In descent, the wearer must decrease system energy on each step by the product of body weight and step height differential. By contrast with ascent, it is possible for a brace to reduce the metabolic cost of descent because a brace can transform the decrease in potential energy into heat, much like the brakes of a bicycle.

As stated earlier, to a first order, for a system having constant average velocity over any constant slope, the average horizontal component of the GRF must be zero and the average vertical component of GRF must equal body weight. This implies that if we add the vertical component of average velocity times time to the vertical position of the torso mass, all equations of motion governing dynamic behavior of the system are satisfied. Thus from the perspective of the torso mass residing at the hip socket, to a first order, the leg thrust force during each step is dictated by the chosen gait parameters and is not dependent on terrain slope. From the perspective of the support and swing legs, however, sloped walking is substantially different than zero slope walking because a fully extended leg cannot transfer the GRF to the hip socket when the distance between hip and ground point of the extended Seg is greater than leg length.

Figure 22A:
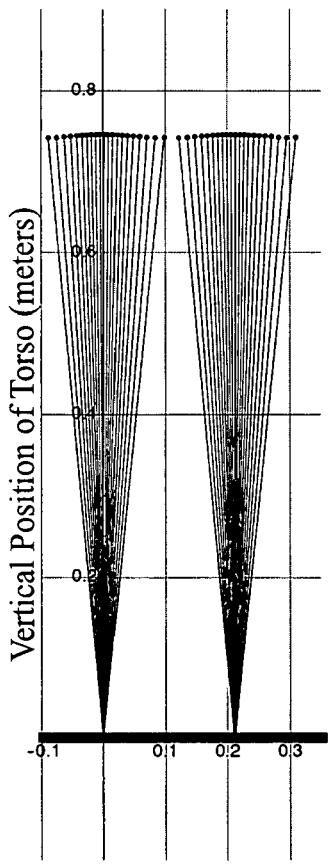
FIGS. 22A-22C show the position of the torso and Seg at 40 millisecond intervals over two successive steps walking on level ground, on ascending stairs and on descending stairs.
Figure 22B:
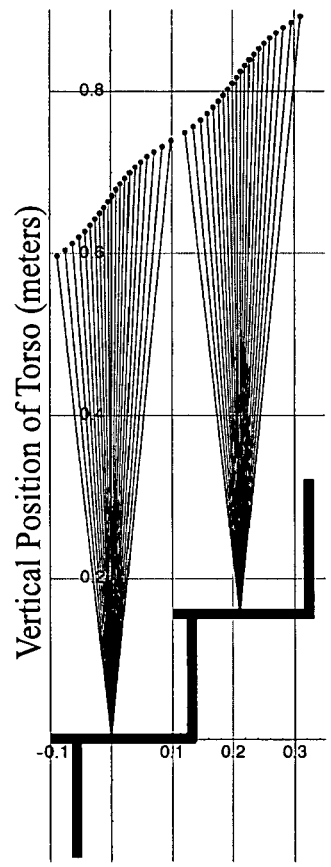
Figure 22C:
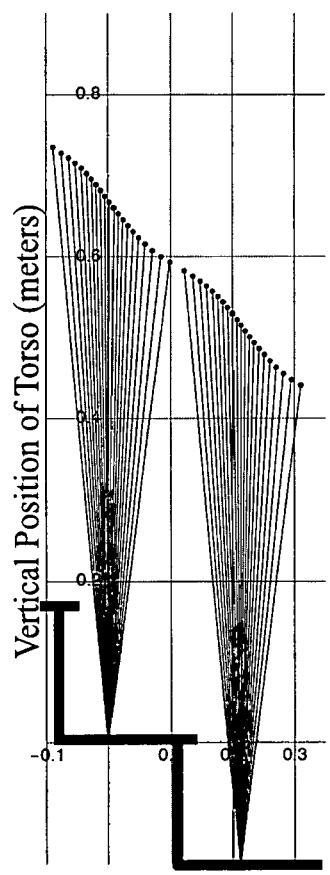

FIGS. 22A-22C show the position of the torso and Seg at 40 millisecond intervals over two successive steps walking over level ground, ascending stairs and descending stairs. FIG. 22A shows the torso position and Seg at 40 milliseconds intervals over two successive steps on level ground. In this system simulation, the step length is 0.211 meters and the step period is 0.858 seconds. This step length and period corresponds to walking up or down stairs. FIG. 22B shows the torso and Seg ascending stairs with a vertical ascent rate of 0.177 meters per second. As can be seen, to achieve stair ascent, the leg at heelstrike must be flexed sufficiently to allow the GRF to be transferred to the hip socket through a shortened Seg. This implies that the quadriceps of the wearer must supply the needed $F_{thrust}$ 32 force while the distance between hip and ankle is increasing thereby introducing energy into the torso. FIG. 22C shows the torso and Seg descending stairs with a vertical descent rate of 0.177 meters per second. In descent, the leg at heelstrike is fully extended. During the support epoch, the support leg must supply the needed $F_{thrust}$ 32 force while the distance between hip and ankle is decreasing thereby extracting energy from the torso. Note that the knee spring reaches maximum torsion in nine milliseconds and remains frozen for 98% of the step period. A novel aspect of an embodiment of the invention allows the required $F_{thrust}$ 32 force to be generated by braking in descent, as well as quadricep action by the user in ascent, regardless of the action of the knee spring freezing mechanism.

Humans create a mental model of the terrain in their near forward path and initiate nerve pulses to control both foot placement of the swing leg and muscles contraction forces of the support leg. The footprint placement of each step is based on learned response in past similar situations. For a person wearing a knee brace, especially over complex terrain paths, it is extremely important that the device assist but not impede. Control of the knee joint is well known to be one of the most challenging problems facing inventors. The control problem for one leg can be partitioned into a swing phase and a support phase since the two phases naturally alternate.

The leg swing phases consists of two subphases. During the flexion subphase the knee angle monotonically increases. During the following extension subphase, the knee monotonically decreases. The flexion subphase starts when the pressure of the wearer's foot against shoe insole drops to zero. At the start of this subphase, the swing leg is still rotating backward. Following toeoff, the person quickly provides angular acceleration hip torque to stop the backward rotation and begin forward rotation. To prevent the swing leg foot from hitting the ground, the person also flexes his knee and dorsiflexes his ankle. Experimentally, it has been determined that if the thigh clutch can transition at the beginning of the flexion subphase from its actuated state to its released state in less than 20 milliseconds, the wearer does not sense the transition. The extension subphase begins at that point in the gait cycle when the swing leg ankle is approximately directly beneath the hip socket. During this subphase, the person extends the knee and plantarflexes the ankle in preparation for the heelstrike of the swing leg. These swing leg constraints imposed requirements on the thigh clutch actuator mechanism. In particular, a means for detecting when the flexion swing subphase begins based on pressure is required. Secondly, the transition from activated to released state must occur in less than 20 milliseconds. Thirdly, the transition from released to fully activated states must occur within the extension swing subphase. Since the swing subphase is approximately equal to half the step period, the thigh clutch actuator must transition from its released state to its activated state in approximately 160 milliseconds.

On level ground, the extension swing subphase causes reduction of the knee angle to near zero. When walking uphill, the maximum knee angle during flexion swing subphase is substantially larger than on level ground and the knee angle at the end of the extension swing subphase is greater than zero. When walking downhill, the knee angle of the swing leg at the start of the flexion subphase is substantially greater than zero with the knee angle at the end of the extension subphase being near zero. By knowing the knee angle and angle that the shank frame 2 makes with the gravitational force vector, it is straightforward to determine whether the person is intending to place the swing foot uphill, downhill or at the same level as the support foot.

Support phase of a leg is characterized by full body weight being applied by the heel of the new support leg at heelstrike. At heelstrike, the new support leg is fully extended for downhill and level terrain walking and flexed in uphill walking. For uphill walking, the wearer's quadriceps muscles are naturally activated through the support epoch and the only control issue is to allow the unimpeded extension of the flexed support leg. When walking on level ground, the only control issue is the release of the knee spring energy at the proper point in time. In downhill walking and stair descent, the new support leg is fully extended at heel strike and ends the support phase by being partially flexed. This requires that the braced support leg must supply torque while the knee angle is increasing. While an embodiment of the invention allows this action to occur, the control problem is knowing the rate at which energy should be dissipated and when thigh clutch slipping should be allowed. In level walking and uphill walking, the rate of energy dissipation by the knee brace is essentially zero. In downhill walking, the rate of energy dissipation is non zero and dependent upon the wearer's intent.

For the case of a person walking downstairs at constant rate, the fact that the person is descending and the rate of descent can be computed during the prior swing phase of the new braced support leg. The problem occurs when the desire to change gaits is a surprise to the control system. For example, the person at the top of a set of stairs pauses with body weight supported by one braced and one unbraced leg. If the first downstairs step is with the braced leg, the control system of the braced leg can determine the rate of descent. If however the first downstairs step is with the unbraced leg, the control system of the braced leg cannot determine the rate of energy dissipation because it has no means for sensing how fast the person wants to walk down the stairs.

Solving this wearer intent control problem is straightforward after it is recognized that it arises only the wearer's intent cannot be computed during the swing phase of a braced leg prior to its support phase. In one solution, the wearer signals a non-zero rate of energy dissipation just prior to downhill descent via an explicit command. For example, pressure pads under the large and small toes of the support leg can be used to specify descent mode with a configurable rate of energy dissipation. In another solution, a configurable rate of energy dissipation is assumed whenever the gait state is such that the rate of energy dissipation cannot be determined. The rate of energy dissipation is then decreased to zero during the swing phase of a braced support leg prior to heelstrike. This scheme results in unbraced action only on gait transitions. Note that both explicit and implicit support control of support leg dissipation can exist simultaneously since the wearer can override the implicit mode of operation with explicit commands.

While this invention has been particularly shown and described with references to preferred embodiments thereof, it will be understood by those skilled in the art that various changes in form and details may be made therein without departing from the scope of the invention encompassed by the appended claims.

What is claimed is:

1. A metabolically efficient leg brace, comprising:
   a shank frame for transferring forces between a wearer's tibia/fibula and the shank frame;
   a thigh frame for transferring forces between a wearer's femur and the thigh frame;
   at least one knee joint rotatably coupling the shank frame to the thigh frame;
   at least one torsion spring having a torsional axis at the at least one knee joint, a first arm of the torsion spring coupled to the shank frame, and a second arm of the torsion spring coupled to an input arbor of a thigh clutch;
   an output arbor of the thigh clutch coupled to the thigh frame;
   a first activation mechanism for actuating and releasing the thigh clutch; and
   an electronics control module controlling the first activation mechanism during periods governed by the wearer's gait.

2. The leg brace of claim 1, further comprising: a shoe frame rotatably coupled to the shank frame at an ankle joint for transferring forces between the wearer's shoe/foot and the shoe frame.

3. The leg brace of claim 1, further comprising:
   a second leg brace; and
   an attached mass support frame rotatably coupled at a hip joint to respective thigh frames of each leg brace for transmitting forces between attached masses and the coupled leg braces.

4. The leg brace of claim 1, wherein the first activation mechanism is a cam optimized for reduced energy consumption.

5. A metabolically efficient leg brace, comprising:
   a shank frame for transferring forces between a wearer's tibia/fibula and the shank frame;
   a thigh frame for transferring forces between a wearer's femur and the thigh frame;
   at least one knee joint rotatably coupling the shank frame to the thigh frame;
   at least one torsion spring having a torsional axis at the at least one knee joint, a first arm of the torsion spring coupled to the shank frame, and a second arm of the torsion spring coupled to an input arbor of a thigh clutch;
   an output arbor of the thigh clutch coupled to the thigh frame; and
   a first activation mechanism for actuating and releasing the thigh clutch during periods governed by the wearer's gait;
   a spring clutch having an input arbor coupled to the first arm of the at least one torsion spring and an output arbor coupled to the shank frame; and
   a second activation mechanism for actuating and releasing the spring clutch during periods governed by the wearer's gait.

6. The leg brace of claim 5, wherein the spring clutch is a one-way clutch with an orientation selected such that its free direction of rotation occurs during the wearer's knee flexion.

7. The leg brace of claim 5, wherein the clutch is a one-way two-state clutch with an orientation selected such that its direction of rotation occurs during the wearer's knee flexion.

8. The leg brace of claim 5, wherein the second activation mechanism is a cam optimized for reduced energy consumption.

9. The leg brace of claim 5, wherein the at least one torsion spring is a non-linear hardening torsion spring.

10. The leg brace of claim 5, wherein the thigh clutch is a one-way two-state clutch whose hard direction occurs during a wearer's knee flexion.

11. The leg brace of claim 5, wherein the first activation mechanism is a cam optimized for reduced energy consumption.

12. A metabolically efficient leg brace, comprising:
    a shank frame for transferring forces between a wearer's tibia/fibula and the shank frame;
    a thigh frame for transferring forces between a wearer's femur and the thigh frame;
    at least one knee joint rotatably coupling the shank frame to the thigh frame;
    at least one torsion spring having a torsional axis at the at least one knee joint, a first arm of the torsion spring coupled to the shank frame, and a second arm of the torsion spring coupled to an input arbor of a thigh clutch;
    an output arbor of the thigh clutch coupled to the thigh frame; and
    a first activation mechanism for actuating and releasing the thigh clutch during periods governed by the wearer's gait; wherein the thigh clutch transfers torque between slipping input and output arbors of the thigh clutch and the activation mechanism activates the thigh clutch to achieve constant power dissipation.

13. A metabolically efficient leg brace, comprising:
    a shank frame for transferring forces between a wearer's tibia/fibula and the shank frame;
    a thigh frame for transferring forces between a wearer's femur and the thigh frame;
    at least one knee joint rotatably coupling the shank frame to the thigh frame;
    at least one torsion spring having a torsional axis at the at least one knee joint, a first arm of the torsion spring coupled to the shank frame, and a second arm of the torsion spring coupled to an input arbor of a thigh clutch;
    an output arbor of the thigh clutch coupled to the thigh frame; and
    a first activation mechanism for actuating and releasing the thigh clutch during periods governed by the wearer's gait.

* * * * *